US012642654B2

(12) United States Patent
Yellin et al.

(10) Patent No.: US 12,642,654 B2
(45) Date of Patent: Jun. 2, 2026

(54) TRANSCATHETER ANNULOPLASTY SYSTEM AND METHODS

(71) Applicant: Valcare Medical, Inc., Wilmington, DE (US)

(72) Inventors: Nadav Yellin, Aven Yehuda (IL); Yoav Rozen, Binyamina (IL); Yuri Falkovich, Pardes Hana (IL)

(73) Assignee: Valcare Medical, Inc., Wilmington, DE (US)

( * ) Notice: Subject to any disclaimer, the term of this patent is extended or adjusted under 35 U.S.C. 154(b) by 0 days.

(21) Appl. No.: 19/363,425

(22) Filed: Oct. 20, 2025

(65) Prior Publication Data

US 2026/0108352 A1     Apr. 23, 2026

Related U.S. Application Data

(60) Provisional application No. 63/709,798, filed on Oct. 21, 2024.

(51) Int. Cl.
A61F 2/24 (2006.01)

(52) U.S. Cl.
CPC .......... A61F 2/2448 (2013.01); A61F 2/2466 (2013.01); *A61F 2220/0016* (2013.01); *A61F 2230/0065* (2013.01)

(58) Field of Classification Search
CPC .............................. A61F 2/2442; A61F 2/2448
See application file for complete search history.

(56) References Cited

U.S. PATENT DOCUMENTS

| | | | |
|---|---|---|---|
| 4,164,046 A | 8/1979 | Cooley | |
| 4,602,911 A | 7/1986 | Ahmadi et al. | |
| 4,874,378 A | 10/1989 | Hillstead | |
| (Continued) | | | |

FOREIGN PATENT DOCUMENTS

| | | | |
|---|---|---|---|
| CN | 2114422 U | 9/1992 | |
| CN | 2633218 Y | 8/2004 | |
| (Continued) | | | |

OTHER PUBLICATIONS

EP Extended Search Report dated May 23, 2025, in EP Patent Application Serial No. 22855660.1.
(Continued)

*Primary Examiner* — Brian A Dukert
(74) *Attorney, Agent, or Firm* — Greenberg Traurig, LLP; Christopher C. Bolten; Robert D. Ward

(57) ABSTRACT

Systems and methods are provided for an annuloplasty device and delivery system for treating valvular regurgitation. The annuloplasty device (e.g., a transcatheter annuloplasty ring) may include a tube having anterior and posterior anchors that may transition from a constrained state within the tube to a deployed state in which anchors extend through windows of the tube into tissue at the native valve site. Each anchor may include valvular and atrial anchors as well as anchors having different shapes (e.g., a curved anchor and a non-curved anchor). The annuloplasty device may be delivered to the native valve site via a catheter and the annuloplasty device may be manipulated within the patient's heart using a delivery handle to selectively deploy anchors while closing the anterior-to-posterior distance of the valve to treat valvular regurgitation.

23 Claims, 15 Drawing Sheets

(56) References Cited

U.S. PATENT DOCUMENTS

| | | | |
|---|---|---|---|
| 4,953,540 | A | 9/1990 | Ray et al. |
| 5,080,662 | A | 1/1992 | Paul |
| 5,236,440 | A | 8/1993 | Hlavacek |
| 5,306,296 | A | 4/1994 | Wright et al. |
| D376,206 | S | 12/1996 | Reif |
| 5,609,565 | A | 3/1997 | Nakamura |
| 5,695,518 | A | 12/1997 | Laerum |
| 5,716,370 | A | 2/1998 | Williamson, IV et al. |
| 5,855,614 | A | 1/1999 | Stevens et al. |
| D410,543 | S | 6/1999 | Reif |
| 6,113,611 | A | 9/2000 | Allen et al. |
| 6,231,602 | B1 | 5/2001 | Carpentier et al. |
| 6,447,524 | B1 | 9/2002 | Knodel et al. |
| D471,981 | S | 3/2003 | Reif |
| 6,619,291 | B2 | 9/2003 | Hlavka et al. |
| 6,629,534 | B1 | 10/2003 | St. et al. |
| 6,669,687 | B1 | 12/2003 | Saadat |
| 6,689,048 | B2 | 2/2004 | Vanden Hoek et al. |
| 6,726,704 | B1 | 4/2004 | Loshakove et al. |
| 6,776,784 | B2 | 8/2004 | Ginn |
| 6,790,229 | B1 | 9/2004 | Berreklouw |
| 6,797,002 | B2 | 9/2004 | Spence et al. |
| 6,805,711 | B2 | 10/2004 | Quijano et al. |
| 6,869,444 | B2 | 3/2005 | Gabbay |
| 6,893,459 | B1 | 5/2005 | Macoviak |
| 7,101,395 | B2 | 9/2006 | Tremulis et al. |
| 7,114,953 | B1 | 10/2006 | Wagner |
| 7,175,660 | B2 | 2/2007 | Cartledge et al. |
| 7,238,191 | B2 | 7/2007 | Bachmann |
| 7,285,087 | B2 | 10/2007 | Moaddeb et al. |
| 7,297,150 | B2 | 11/2007 | Cartledge et al. |
| 7,569,072 | B2 | 8/2009 | Berg et al. |
| 7,594,887 | B2 | 9/2009 | Moaddeb et al. |
| 7,635,329 | B2 | 12/2009 | Goldfarb et al. |
| 7,655,040 | B2 | 2/2010 | Douk et al. |
| 7,717,954 | B2 | 5/2010 | Solem et al. |
| 7,722,668 | B2 | 5/2010 | Moaddeb et al. |
| 7,758,637 | B2 | 7/2010 | Starksen et al. |
| 7,828,819 | B2 | 11/2010 | Webler et al. |
| 7,837,729 | B2 | 11/2010 | Gordon et al. |
| D642,683 | S | 8/2011 | Drake |
| 7,988,725 | B2 | 8/2011 | Gross et al. |
| 8,163,014 | B2 | 4/2012 | Lane et al. |
| 8,182,529 | B2 | 5/2012 | Gordon et al. |
| 8,236,049 | B2 | 8/2012 | Rowe et al. |
| 8,287,591 | B2 | 10/2012 | Keidar et al. |
| 8,333,204 | B2 | 12/2012 | Saadat |
| 8,518,107 | B2 | 8/2013 | Tsukashima et al. |
| 8,579,968 | B1 | 11/2013 | Shannon et al. |
| 8,690,939 | B2 | 4/2014 | Miller et al. |
| 8,821,570 | B2 | 9/2014 | DuMONTELLE et al. |
| 9,107,749 | B2 * | 8/2015 | Bobo ................... A61F 2/2445 |
| 9,180,008 | B2 | 11/2015 | Yellin et al. |
| 9,402,721 | B2 | 8/2016 | Buchbinder et al. |
| 9,433,503 | B2 | 9/2016 | Tsukashima et al. |
| 9,839,519 | B2 | 12/2017 | Shaolian et al. |
| 9,877,833 | B1 | 1/2018 | Bishop et al. |
| D858,771 | S | 9/2019 | Kugler et al. |
| 10,405,979 | B2 | 9/2019 | Schaffner et al. |
| 10,543,087 | B2 | 1/2020 | Yellin et al. |
| 10,779,945 | B2 | 9/2020 | Buchbinder et al. |
| 11,058,417 | B2 | 7/2021 | Foerster et al. |
| 11,103,349 | B2 * | 8/2021 | Yellin ................... A61F 2/2448 |
| 11,191,536 | B2 | 12/2021 | Foerster et al. |
| 11,224,422 | B2 | 1/2022 | Foerster et al. |
| 11,298,230 | B2 | 4/2022 | Shaolian et al. |
| 11,382,749 | B2 | 7/2022 | Yellin et al. |
| D964,567 | S | 9/2022 | Ito |
| 11,510,835 | B2 | 11/2022 | Yellin et al. |
| 11,534,300 | B2 | 12/2022 | Yellin et al. |
| 11,571,301 | B2 | 2/2023 | Yellin et al. |
| 11,571,307 | B2 | 2/2023 | Yellin et al. |
| 11,576,779 | B2 | 2/2023 | Yellin et al. |
| 11,617,647 | B2 | 4/2023 | Yellin |
| 11,654,018 | B2 | 5/2023 | Shaolian et al. |
| 11,793,628 | B2 | 10/2023 | Dumontelle et al. |
| 11,806,009 | B2 | 11/2023 | Foerster et al. |
| 11,806,237 | B2 | 11/2023 | Rozen et al. |
| 11,813,164 | B2 | 11/2023 | Yellin et al. |
| 11,857,418 | B2 | 1/2024 | Yellin et al. |
| 12,115,069 | B2 | 10/2024 | Shaolian et al. |
| 12,127,941 | B2 | 10/2024 | Yellin et al. |
| 12,279,955 | B2 | 4/2025 | Yellin et al. |
| 12,396,853 | B2 | 8/2025 | Colli et al. |
| 12,409,034 | B2 | 9/2025 | Colli et al. |
| 2001/0049557 | A1 | 12/2001 | Chinn et al. |
| 2002/0026214 | A1 | 2/2002 | Tanner et al. |
| 2002/0151961 | A1 | 10/2002 | Lashinski et al. |
| 2002/0151970 | A1 | 10/2002 | Garrison et al. |
| 2002/0188170 | A1 | 12/2002 | Santamore et al. |
| 2002/0198526 | A1 | 12/2002 | Shaolian et al. |
| 2003/0050649 | A1 | 3/2003 | Brock et al. |
| 2003/0050693 | A1 | 3/2003 | Quijano et al. |
| 2003/0078465 | A1 | 4/2003 | Pai et al. |
| 2003/0078671 | A1 | 4/2003 | Lesniak et al. |
| 2003/0191528 | A1 | 10/2003 | Quijano et al. |
| 2003/0198605 | A1 | 10/2003 | Montgomery |
| 2003/0199974 | A1 | 10/2003 | Lee et al. |
| 2004/0044364 | A1 | 3/2004 | DeVries et al. |
| 2004/0068276 | A1 | 4/2004 | Golden et al. |
| 2004/0073237 | A1 | 4/2004 | Leinsing |
| 2004/0122514 | A1 | 6/2004 | Fogarty et al. |
| 2004/0138744 | A1 | 7/2004 | Lashinski et al. |
| 2004/0148021 | A1 | 7/2004 | Cartledge et al. |
| 2004/0193191 | A1 | 9/2004 | Starksen et al. |
| 2004/0243230 | A1 | 12/2004 | Navia et al. |
| 2004/0249391 | A1 | 12/2004 | Cummins |
| 2004/0260393 | A1 | 12/2004 | Rahdert et al. |
| 2004/0260394 | A1 | 12/2004 | Douk et al. |
| 2005/0004668 | A1 | 1/2005 | Aklog et al. |
| 2005/0020696 | A1 | 1/2005 | Montgomery et al. |
| 2005/0033325 | A1 | 2/2005 | May et al. |
| 2005/0065550 | A1 | 3/2005 | Starksen et al. |
| 2005/0090846 | A1 | 4/2005 | Pedersen et al. |
| 2005/0096740 | A1 | 5/2005 | Langberg et al. |
| 2005/0113910 | A1 | 5/2005 | Paniagua et al. |
| 2005/0137692 | A1 | 6/2005 | Haug et al. |
| 2005/0137695 | A1 | 6/2005 | Salahieh et al. |
| 2005/0203549 | A1 | 9/2005 | Realyvasquez |
| 2005/0222678 | A1 | 10/2005 | Lashinski et al. |
| 2005/0240200 | A1 | 10/2005 | Bergheim |
| 2005/0250161 | A1 | 11/2005 | Suciu-Foca et al. |
| 2005/0267572 | A1 | 12/2005 | Schoon et al. |
| 2005/0283190 | A1 | 12/2005 | Huitema et al. |
| 2005/0288778 | A1 | 12/2005 | Shaoulian et al. |
| 2005/0288781 | A1 | 12/2005 | Moaddeb et al. |
| 2006/0009737 | A1 | 1/2006 | Whiting et al. |
| 2006/0020327 | A1 | 1/2006 | Lashinski et al. |
| 2006/0020334 | A1 | 1/2006 | Lashinski et al. |
| 2006/0052867 | A1 | 3/2006 | Revuelta et al. |
| 2006/0122633 | A1 | 6/2006 | To et al. |
| 2006/0129025 | A1 | 6/2006 | Levine et al. |
| 2006/0155165 | A1 | 7/2006 | Vanden Hoek et al. |
| 2006/0161169 | A1 | 7/2006 | Nieminen et al. |
| 2006/0184240 | A1 | 8/2006 | Jimenez et al. |
| 2006/0184242 | A1 | 8/2006 | Lichtenstein |
| 2006/0195134 | A1 | 8/2006 | Crittenden |
| 2006/0195183 | A1 | 8/2006 | Navia et al. |
| 2006/0241748 | A1 | 10/2006 | Lee et al. |
| 2006/0282161 | A1 | 12/2006 | Huynh et al. |
| 2007/0016287 | A1 | 1/2007 | Cartledge et al. |
| 2007/0027533 | A1 | 2/2007 | Douk |
| 2007/0038296 | A1 | 2/2007 | Navia |
| 2007/0051377 | A1 | 3/2007 | Douk et al. |
| 2007/0067027 | A1 | 3/2007 | Moaddeb et al. |
| 2007/0073098 | A1 | 3/2007 | Lenker et al. |
| 2007/0080188 | A1 | 4/2007 | Spence et al. |
| 2007/0093854 | A1 | 4/2007 | Kayan |
| 2007/0118215 | A1 | 5/2007 | Moaddeb |
| 2007/0128132 | A1 | 6/2007 | Piergallini et al. |
| 2007/0135913 | A1 | 6/2007 | Moaddeb et al. |
| 2007/0142907 | A1 | 6/2007 | Moaddeb et al. |
| 2007/0213812 | A1 | 9/2007 | Webler et al. |
| 2007/0233239 | A1 | 10/2007 | Navia et al. |

(56)                    References Cited

U.S. PATENT DOCUMENTS

| | | |
|---|---|---|
| 2007/0239272 A1 | 10/2007 | Navia et al. |
| 2007/0244553 A1 | 10/2007 | Rafiee et al. |
| 2007/0244554 A1 | 10/2007 | Rafiee et al. |
| 2007/0244555 A1 | 10/2007 | Rafiee et al. |
| 2007/0244556 A1 | 10/2007 | Rafiee et al. |
| 2007/0250161 A1 | 10/2007 | Dolan |
| 2007/0293942 A1 | 12/2007 | Mirzaee |
| 2008/0039934 A1 | 2/2008 | Styrc |
| 2008/0051807 A1 | 2/2008 | St. Goar et al. |
| 2008/0065011 A1 | 3/2008 | Marchand et al. |
| 2008/0177380 A1 | 7/2008 | Starksen et al. |
| 2008/0177381 A1 | 7/2008 | Navia et al. |
| 2008/0200980 A1 | 8/2008 | Robin et al. |
| 2008/0208327 A1 | 8/2008 | Rowe |
| 2008/0215145 A1 | 9/2008 | Moaddeb et al. |
| 2008/0243220 A1 | 10/2008 | Barker |
| 2008/0262513 A1 | 10/2008 | Stahler et al. |
| 2008/0262609 A1 | 10/2008 | Gross et al. |
| 2008/0288060 A1 | 11/2008 | Kaye et al. |
| 2008/0306586 A1 | 12/2008 | Cartledge et al. |
| 2009/0076599 A1 | 3/2009 | Bergin |
| 2009/0088838 A1 | 4/2009 | Shaolian et al. |
| 2009/0118747 A1 | 5/2009 | Bettuchi et al. |
| 2009/0125098 A1 | 5/2009 | Chuter |
| 2009/0149872 A1 | 6/2009 | Gross et al. |
| 2009/0216322 A1 | 8/2009 | Le et al. |
| 2009/0222083 A1 | 9/2009 | Nguyen et al. |
| 2009/0238778 A1 | 9/2009 | Mordas et al. |
| 2009/0299470 A1 | 12/2009 | Rao et al. |
| 2010/0010616 A1 | 1/2010 | Drews et al. |
| 2010/0030014 A1 | 2/2010 | Ferrazzi |
| 2010/0063586 A1 | 3/2010 | Hasenkam et al. |
| 2010/0076549 A1 | 3/2010 | Keidar et al. |
| 2010/0121433 A1 | 5/2010 | Bolling et al. |
| 2010/0161047 A1 | 6/2010 | Cabiri |
| 2010/0185274 A1 | 7/2010 | Moaddeb et al. |
| 2010/0191327 A1 | 7/2010 | Lane et al. |
| 2010/0204713 A1 | 8/2010 | Ruiz Morales |
| 2010/0211166 A1 | 8/2010 | Miller et al. |
| 2010/0249920 A1 | 9/2010 | Bolling et al. |
| 2010/0262232 A1 | 10/2010 | Annest |
| 2010/0266989 A1 | 10/2010 | Piergallini et al. |
| 2010/0280604 A1 | 11/2010 | Zipory et al. |
| 2010/0280605 A1 | 11/2010 | Hammer et al. |
| 2010/0286767 A1 | 11/2010 | Zipory et al. |
| 2011/0004299 A1 | 1/2011 | Navia et al. |
| 2011/0011917 A1 | 1/2011 | Loulmet |
| 2011/0022168 A1 | 1/2011 | Cartledge |
| 2011/0027753 A1 | 2/2011 | Maurat et al. |
| 2011/0034953 A1 | 2/2011 | Milo |
| 2011/0034999 A1 | 2/2011 | Carpentier et al. |
| 2011/0060407 A1 | 3/2011 | Ketai et al. |
| 2011/0066231 A1 | 3/2011 | Cartledge et al. |
| 2011/0093062 A1 | 4/2011 | Cartledge et al. |
| 2011/0106245 A1 | 5/2011 | Miller et al. |
| 2011/0106247 A1 | 5/2011 | Miller et al. |
| 2011/0137397 A1 | 6/2011 | Chau et al. |
| 2011/0166649 A1 | 7/2011 | Gross et al. |
| 2011/0190879 A1 | 8/2011 | Bobo et al. |
| 2011/0208295 A1 | 8/2011 | Cartledge et al. |
| 2011/0208298 A1 | 8/2011 | Tuval et al. |
| 2011/0224785 A1 | 9/2011 | Hacohen |
| 2011/0257728 A1 | 10/2011 | Kuehn |
| 2011/0282361 A1 | 11/2011 | Miller et al. |
| 2011/0301698 A1 | 12/2011 | Miller et al. |
| 2011/0301699 A1 | 12/2011 | Saadat |
| 2011/0319989 A1 | 12/2011 | Lane et al. |
| 2012/0022557 A1 | 1/2012 | Cabiri et al. |
| 2012/0022639 A1 | 1/2012 | Hacohen et al. |
| 2012/0022644 A1 | 1/2012 | Reich et al. |
| 2012/0053687 A1 | 3/2012 | Migliazza et al. |
| 2012/0059458 A1 | 3/2012 | Buchbinder et al. |
| 2012/0083806 A1 | 4/2012 | Goertzen |
| 2012/0083880 A1 | 4/2012 | Rankin et al. |
| 2012/0095455 A1 | 4/2012 | Rodmond et al. |
| 2012/0123531 A1 | 5/2012 | Tsukashima et al. |
| 2012/0136436 A1 | 5/2012 | Cabiri et al. |
| 2012/0136463 A1 | 5/2012 | Muniz |
| 2012/0165930 A1 | 6/2012 | Gifford, III et al. |
| 2012/0245604 A1 | 9/2012 | Tegzes |
| 2012/0310330 A1 | 12/2012 | Buchbinder et al. |
| 2013/0066342 A1 | 3/2013 | Dell et al. |
| 2013/0087598 A1 | 4/2013 | Surti |
| 2013/0116780 A1 | 5/2013 | Miller et al. |
| 2013/0166022 A1 | 6/2013 | Conklin |
| 2013/0204361 A1 | 8/2013 | Adams et al. |
| 2013/0226289 A1 | 8/2013 | Shaolian et al. |
| 2013/0226290 A1 | 8/2013 | Yellin et al. |
| 2013/0282114 A1 | 10/2013 | Schweich, Jr. et al. |
| 2013/0289718 A1 | 10/2013 | Tsukashima et al. |
| 2013/0289720 A1 | 10/2013 | Dobrilovic |
| 2013/0304197 A1 | 11/2013 | Buchbinder et al. |
| 2014/0005778 A1 | 1/2014 | Buchbinder et al. |
| 2014/0025163 A1 | 1/2014 | Padala et al. |
| 2014/0046433 A1 | 2/2014 | Kovalsky |
| 2014/0058505 A1 | 2/2014 | Bielefeld |
| 2014/0114407 A1 | 4/2014 | Rajamannan |
| 2014/0188130 A1 | 7/2014 | Sanchez et al. |
| 2014/0214157 A1 | 7/2014 | Börtlein et al. |
| 2014/0277411 A1 | 9/2014 | Börtlein et al. |
| 2014/0277420 A1 | 9/2014 | Migliazza et al. |
| 2014/0364939 A1 | 12/2014 | Deshmukh et al. |
| 2015/0073420 A1 | 3/2015 | Bookwalter et al. |
| 2015/0112432 A1 | 4/2015 | Reich et al. |
| 2015/0127093 A1 | 5/2015 | Hosmer et al. |
| 2015/0173897 A1 | 6/2015 | Raanani et al. |
| 2015/0173987 A1 | 6/2015 | Albinmousa et al. |
| 2015/0351903 A1 | 12/2015 | Morriss et al. |
| 2015/0366666 A1 | 12/2015 | Khairkhahan et al. |
| 2016/0022419 A1 | 1/2016 | Yellin et al. |
| 2016/0038286 A1 | 2/2016 | Yellin et al. |
| 2016/0089235 A1 | 3/2016 | Yellin |
| 2016/0100897 A1 | 4/2016 | Avalos et al. |
| 2016/0106420 A1 | 4/2016 | Foerster et al. |
| 2016/0120642 A1 | 5/2016 | Shaolian et al. |
| 2016/0120645 A1 | 5/2016 | Alon |
| 2016/0220371 A1 | 8/2016 | Keane |
| 2016/0270911 A1 | 9/2016 | Ganesan et al. |
| 2016/0331534 A1 | 11/2016 | Buchbinder et al. |
| 2017/0042670 A1 | 2/2017 | Shaolian et al. |
| 2017/0231763 A1 | 8/2017 | Yellin |
| 2017/0258590 A1 | 9/2017 | Khairkhahan |
| 2017/0296340 A1 | 10/2017 | Gross et al. |
| 2017/0325948 A1 | 11/2017 | Wallace et al. |
| 2018/0028387 A1 | 2/2018 | Yellin et al. |
| 2018/0042723 A1 | 2/2018 | Yellin et al. |
| 2018/0098849 A1 | 4/2018 | Yellin et al. |
| 2018/0161160 A1 | 6/2018 | Shaolian et al. |
| 2018/0161161 A1 | 6/2018 | Yellin et al. |
| 2018/0228610 A1 | 8/2018 | Lashinski et al. |
| 2018/0235758 A1 | 8/2018 | Biadillah et al. |
| 2018/0325670 A1 | 11/2018 | De |
| 2019/0053905 A1 | 2/2019 | Alon |
| 2019/0083091 A1 | 3/2019 | Foerster et al. |
| 2019/0083092 A1 | 3/2019 | Foerster et al. |
| 2019/0083239 A1 | 3/2019 | Shaolian et al. |
| 2019/0083240 A1 | 3/2019 | Shaolian et al. |
| 2019/0091022 A1 | 3/2019 | Yellin et al. |
| 2019/0133765 A1 | 5/2019 | Yellin et al. |
| 2020/0069426 A1 | 3/2020 | Conklin et al. |
| 2020/0138577 A1 | 5/2020 | Smolinsky |
| 2020/0163763 A1 | 5/2020 | Zipory et al. |
| 2020/0170799 A1 | 6/2020 | Yellin et al. |
| 2020/0237516 A1 | 7/2020 | Sampson et al. |
| 2020/0330228 A1 | 10/2020 | Anderson et al. |
| 2021/0015609 A1 | 1/2021 | Dumontelle et al. |
| 2021/0085463 A1 | 3/2021 | Yellin et al. |
| 2021/0161662 A1 | 6/2021 | Albes |
| 2021/0346159 A1 | 11/2021 | Keränen |
| 2021/0353417 A1 | 11/2021 | Yellin et al. |
| 2022/0096237 A1 | 3/2022 | Hiorth et al. |
| 2022/0226116 A1 | 7/2022 | Colli et al. |
| 2022/0226771 A1 | 7/2022 | Lipscomb |
| 2023/0040083 A1 | 2/2023 | Gifford, III et al. |

(56) References Cited

U.S. PATENT DOCUMENTS

| | | | |
|---|---|---|---|
| 2023/0045532 A1 | 2/2023 | Galler et al. | |
| 2023/0285148 A1 | 9/2023 | Yellin et al. | |
| 2023/0372086 A1 | 11/2023 | Galler et al. | |
| 2024/0307182 A1 | 9/2024 | Colli et al. | |
| 2025/0114202 A1 | 4/2025 | Whitman et al. | |

FOREIGN PATENT DOCUMENTS

| | | | |
|---|---|---|---|
| CN | 101411632 A | 4/2009 | |
| CN | 101460113 A | 6/2009 | |
| CN | 101553190 A | 10/2009 | |
| CN | 102014797 A | 4/2011 | |
| CN | 102088930 A | 6/2011 | |
| CN | 202859386 U | 4/2013 | |
| CN | 103179920 A | 6/2013 | |
| CN | 103237523 A | 8/2013 | |
| CN | 103735337 A | 4/2014 | |
| CN | 203954080 U | 11/2014 | |
| CN | 108618871 A | 10/2018 | |
| CN | 113855324 A | 12/2021 | |
| CN | 116269941 A | 6/2023 | |
| DE | 102014102653 A1 | 9/2015 | |
| EP | 1752115 A1 | 2/2007 | |
| EP | 2471464 A1 | 7/2012 | |
| EP | 2600799 A2 | 6/2013 | |
| EP | 2928538 A1 | 10/2015 | |
| EP | 2967700 A1 | 1/2016 | |
| EP | 2600799 B1 | 5/2017 | |
| EP | 3213715 A1 | 9/2017 | |
| EP | 2928538 B1 | 11/2018 | |
| FR | 2845889 A1 | 4/2004 | |
| GB | 1496804 A | 1/1978 | |
| GB | 2366319 A | 3/2002 | |
| GB | 2601146 A | 5/2022 | |
| KR | 20040095482 A | 11/2004 | |
| RU | 125062 U1 | 2/2013 | |
| WO | WO-8000673 A1 | 4/1980 | |
| WO | WO-9009153 A1 | 8/1990 | |
| WO | WO-9728745 A1 | 8/1997 | |
| WO | WO-03017874 A1 | 3/2003 | |
| WO | WO-03047467 A1 | 6/2003 | |
| WO | WO-2005046488 A2 | 5/2005 | |
| WO | WO-2007035882 A2 | 3/2007 | |
| WO | WO-2008097999 A2 | 8/2008 | |
| WO | WO-2009052427 A1 | 4/2009 | |
| WO | WO-2009120764 A2 | 10/2009 | |
| WO | WO-2010004546 A1 | 1/2010 | |
| WO | WO-2010085659 A1 | 7/2010 | |
| WO | WO-2011011443 A2 | 1/2011 | |
| WO | WO-2011097355 A2 | 8/2011 | |
| WO | WO-2011154942 A2 | 12/2011 | |
| WO | WO-2012004679 A2 | 1/2012 | |
| WO | WO-2012019052 A2 | 2/2012 | |
| WO | WO-2012038550 A1 | 3/2012 | |
| WO | WO-2012040865 A1 | 4/2012 | |
| WO | WO-2012063228 A1 | 5/2012 | |
| WO | WO-2012095159 A2 | 7/2012 | |
| WO | WO-2012106354 A1 | 8/2012 | |
| WO | WO-2012167095 A2 | 12/2012 | |
| WO | WO-2012177942 A2 | 12/2012 | |
| WO | WO-2013095816 A1 | 6/2013 | |
| WO | WO-2013128436 A1 | 9/2013 | |
| WO | WO-2013130641 A1 | 9/2013 | |
| WO | WO-2013175468 A2 | 11/2013 | |
| WO | WO-2014089424 A1 | 6/2014 | |
| WO | WO-2014145399 A1 | 9/2014 | |
| WO | WO-2014178869 A1 | 11/2014 | |
| WO | WO-2014189509 A1 | 11/2014 | |
| WO | WO-2014190329 A1 | 11/2014 | |
| WO | WO-2014210600 A2 | 12/2014 | |
| WO | WO-2015052629 A1 | 4/2015 | |
| WO | WO-2015132668 A1 | 9/2015 | |
| WO | WO-2016025894 A1 | 2/2016 | |
| WO | WO-2016040526 A1 | 3/2016 | |
| WO | WO-2018035118 A1 | 2/2018 | |
| WO | WO-2018071540 A1 | 4/2018 | |
| WO | WO-2018170424 A1 | 9/2018 | |
| WO | WO-2020117842 A1 | 6/2020 | |
| WO | WO-2020252200 A1 | 12/2020 | |
| WO | WO-2022126249 A1 | 6/2022 | |
| WO | WO-2022172108 A1 | 8/2022 | |
| WO | WO-2022178042 A1 | 8/2022 | |
| WO | WO-2023069494 A1 | 4/2023 | |
| WO | WO-2023228098 A1 | 11/2023 | |

OTHER PUBLICATIONS

Extended European Search Report for European Application No. 11815347.7, mailed Mar. 14, 2016, 10 Pages.
Extended European Search Report for European Application No. 12793292.9, mailed Dec. 1, 2014, 6 Pages.
Extended European Search Report for European Application No. 13755441.6, mailed Mar. 1, 2016, 12 Pages.
Extended European Search Report for European Application No. 13860442.6, mailed Aug. 11, 2016, 7 pages.
Extended European Search Report for European Application No. 13885021.9, mailed Jan. 3, 2017, 8 Pages.
Extended European Search Report for European Application No. 14762806.9, mailed Jul. 29, 2016, 7 Pages.
Extended European Search Report for European Application No. 14801009.3, mailed Dec. 5, 2016, 8 Pages.
Extended European Search Report for European Application No. 14817662.1, mailed Jan. 23, 2017, 7 Pages.
Extended European Search Report for European Application No. 17155803.4, mailed Aug. 9, 2017, 10 Pages.
Extended European Search Report for European Application No. 17835256.3, mailed Feb. 12, 2020, 9 Pages.
Extended European Search Report for European Application No. 17841988.3, mailed Dec. 16, 2019, 8 Pages.
Extended European Search Report for European Application No. 17860901.2, mailed Jun. 5, 2020, 06 Pages.
Extended European Search Report for European Application No. 18768197.8, mailed Oct. 19, 2020, 7 Pages.
Extended European Search Report for European Application No. 19151726.7, mailed Jul. 22, 2019, 9 Pages.
Extended European Search Report for European Application No. 19170261.2, mailed Aug. 5, 2019, 9 pages.
Extended European Search Report for European Application No. 19893113.1, mailed Nov. 17, 2022, 7 Pages.
Extended European Search Report for European Application No. 20206790.6, mailed Dec. 7, 2020, 9 Pages.
Extended European Search Report for European Application No. 20209605.3, mailed Mar. 9, 2021, 7 pages.
Extended European Search Report for European Application No. 20823198.5, mailed May 15, 2023, 15 Pages.
Extended European Search Report for European Application No. 20823682.8, mailed Apr. 14, 2023, 10 Pages.
Extended European Search Report for European Application No. 20841346.8, mailed Jul. 21, 2023, 9 Pages.
Extended European Search Report for European Application No. 21870447.6, mailed Nov. 11, 2024, 9 Pages.
Extended European Search Report for European Application No. 24215515.8, mailed Feb. 11, 2025—11 Pages.
Extended European Search Report for European Application No. 24219902.4, mailed Mar. 26, 2025—9 Pages.
International Search Report & Written Opinion dated Jul. 24, 2024 in Int'l PCT Patent Appl. Serial No. PCT/US2024/019797.
International Search Report and Written Opinion for International Application No. PCT/IL2022/050868, mailed Nov. 17, 2022, 19 Pages.
International Search Report and Written Opinion for International Application No. PCT/IL2023/050527, mailed Aug. 8, 2023, 14 Pages.
International Search Report and Written Opinion for International Application No. PCT/US2011/046659, mailed Jun. 4, 2012, 13 Pages.

(56)          References Cited

OTHER PUBLICATIONS

International Search Report and Written Opinion for International Application No. PCT/US2012/040481, mailed Dec. 6, 2012, 12 Pages.
International Search Report and Written Opinion for International Application No. PCT/US2013/028065, mailed Jun. 27, 2013, 11 Pages.
International Search Report and Written Opinion for International Application No. PCT/US2013/042275, mailed Feb. 20, 2014, 18 Pages.
International Search Report and Written Opinion for International Application No. PCT/US2013/058102, mailed Apr. 21, 2014, 10 Pages.
International Search Report and Written Opinion for International Application No. PCT/US2013/073552, mailed Mar. 6, 2014, 10 Pages.
International Search Report and Written Opinion for International Application No. PCT/US2014/030163, mailed Aug. 27, 2014, 10 Pages.
International Search Report and Written Opinion for International Application No. PCT/US2014/039454, mailed Oct. 22, 2014, 11 Pages.
International Search Report and Written Opinion for International Application No. PCT/US2014/044920, mailed Dec. 24, 2014, 15 Pages.
International Search Report and Written Opinion for International Application No. PCT/US2017/044129, mailed Sep. 27, 2017, 9 Pages.
International Search Report and Written Opinion for International Application No. PCT/US2017/046933, mailed Dec. 21, 2017, 11 Pages.
International Search Report and Written Opinion for International Application No. PCT/US2017/056138, mailed Jan. 8, 2018 , 6 Pages.
International Search Report and Written Opinion for International Application No. PCT/US2018/022910, mailed May 23, 2018, 7 Pages.
International Search Report and Written Opinion for International Application No. PCT/US2019/064289, mailed Feb. 5, 2020, 8 Pages.
International Search Report and Written Opinion for International Application No. PCT/US2020/037294, mailed Aug. 28, 2020, 8 Pages.
International Search Report and Written Opinion for International Application No. PCT/US2020/037296, mailed Sep. 10, 2020, 8 Pages.
International Search Report and Written Opinion for International Application No. PCT/US2020/042201, mailed Oct. 9, 2020, 7 Pages.
International Search Report and Written Opinion for International Application No. PCT/US2021/071467, mailed Jan. 14, 2022, 12 Pages.
International Search Report and Written Opinion for International Application No. PCT/US2021/071468, mailed Jan. 19, 2022, 8 Pages.
Mitral Valve Repair Annuloplasty Rings: Surgeon Q&A with Dr. Steve Bolling], YouTube.com, Posted: Oct. 10, 2017[online], site visited: [Apr. 29, 2025], URL:https://www.youtube.com/watch?v=Pq4SE_iVbf0. (Year: 2021).
Partial Supplementary European Search Report for European Application No. 11815347.7, mailed Nov. 16, 2015, 06 Pages.
Partial Supplementary European Search Report for European Application No. 13755441.6, mailed Nov. 3, 2015, 7 Pages.
[Valcare Medical Announces First-in-Human Transseptal Implant of the AMEND™ Annuloplasty Ring for Mitral Valve Repair], techwald.com, by [HERZLIYA, Israel], Published: [Jan. 27, 2021] [online], site visited: [Apr. 29, 2025], URL: (Year: 2021].

\* cited by examiner

TRANSCATHETER ANNULOPLASTY SYSTEM AND METHODS

CROSS-REFERENCE TO RELATED APPLICATIONS

This application claims priority to U.S. Provisional Application Ser. No. 63/709,798, filed Oct. 21, 2024, the entire contents of which are incorporated herein by reference.

TECHNICAL FIELD

This technology relates, in general, to an annuloplasty system and methods, for example, an annuloplasty system for transcatheter implantation of an annuloplasty ring at a native heart valve for the treatment of valvular regurgitation.

BACKGROUND

Mitral Regurgitation is a valvular dysfunction that causes blood volume to flow during systole (during left ventricular contraction) from the left ventricle to the left atrium. In contrast, in a healthy heart, this direction of flow is blocked by the mitral valve. The reverse flow during systole causes pressure to rise in the left atrium, and maintaining a normal cardiac output results in an increased pressure in the left ventricle.

Treating patients with MR (mitral regurgitation) or TR (tricuspid regurgitation) could require valve replacement in order to reduce or eliminate the regurgitation. For many years, the commonly accepted treatment was surgical repair or replacement of the native valve during open heart surgery. In recent years, a transcatheter technique has been developed for introducing and implanting a prosthetic heart valve using a flexible catheter in a manner that is less invasive than open heart surgery with fewer risks of complications.

In the transcatheter technique, a prosthetic device is delivered to the native valve site (e.g., aortic valve, mitral valve, or tricuspid valve) through a catheter while the device is constrained in a shaft with a reduced diameter. The device is then expanded when it is delivered to the correct position at the native valve site. Examples of such prosthetic devices for treating valvular regurgitation, and related processes for delivering the prosthetics through a catheter, are described in U.S. Pat. No. 8,518,107 to Tsukashima et al., U.S. Pat. No. 10,543,087 to Yellin et al., U.S. Pat. No. 11,103,349 to Yellin et al., U.S. Pat. No. 11,534,300 to Yellin et al., U.S. Pat. No. 11,576,779 to Yellin et al., U.S. Pat. No. 11,806,237 to Rozen et al., U.S. Pat. No. 11,857,418 to Yellin et al., the entire contents of each of which are incorporated herein by reference.

Advancing the catheter to the target site can be achieved through: (a) the vascular system where a catheter is advanced from the femoral vein/artery, or any other blood vessel that allows access to the target site; (b) trans-apically where a catheter is advanced through a small incision made in the chest wall and then through the apex; or (c) trans-atrially where a catheter is advanced through a small incision made in the chest wall and then through the left or right atrium, for example.

While valves and other prosthetic devices are capable of transcatheter delivery and implantation at the native valve site, transcatheter devices for treating valvular regurgitation often are difficult to secure to the native valve tissue. More specifically, transitioning anchors from a constrained state to a deployed state during transcatheter delivery in a manner sufficient to firmly secure the prosthetic at the native valve site is a significant challenge. Additionally, reducing the anterior-posterior distance of the native valve during transcatheter implantation of the prosthetic has proven to be difficult due the constraints of transcatheter delivery.

Accordingly, there is a need for improved annuloplasty devices, systems, and methods for treating valvular regurgitation having enhanced features for securing the annuloplasty device to the native valve and reducing the anterior-posterior distance of the valve.

SUMMARY

Provided herein are systems and methods for an annuloplasty device and delivery system for treating valvular regurgitation. The annuloplasty device (e.g., a transcatheter annuloplasty ring) may include a tube having anterior and posterior anchors having anchors with different shapes (e.g., curved anchors and a linear and/or non-curved anchor). The anterior and posterior anchors may transition from a constrained state within the tube to a deployed state in which anchors extend through windows of the tube into tissue at the native valve site to secure the annuloplasty device to the native valve. Each anchor may include valvular and atrial anchors such that the annuloplasty device may be secured to both valvular and atrial tissue. The annuloplasty device may be delivered to the native valve site via a catheter and the annuloplasty device may be manipulated within the patient's heart to selectively deploy anchors to close the anterior-to-posterior distance of the valve thereby treating valvular regurgitation.

An annuloplasty device is provided herein and may include a tube having a first end, a second end, an inner lumen, a first plurality of windows, and a second plurality of windows, the first plurality of windows designed to be orientated toward anterior tissue of a native valve and a second plurality of windows designed to be orientated toward posterior tissue of the native valve when the annuloplasty device is implanted at a native valve site, at least one anterior anchor having a first elongated base, a first plurality of anchors extending from the first elongated base, each anchor of the first plurality of anchors having a first shape, and at least one first anchor extending from the first elongated base and having a second shape different than the first shape, the at least one anterior anchor designed to transition from a first constrained state fully disposed within the tube to a first deployed state in which the first plurality of anchors and the at least one first anchor extend through at least some of the first plurality of windows into the anterior tissue of the native valve, at least one posterior anchor having a second elongated base, a second plurality of anchors extending from the second elongated base, each anchor of the second plurality of anchors having a third shape, and at least one second anchor extending from the second elongated base and having a fourth shape different than the third shape, the at least one posterior anchor designed to transition from a second constrained state fully disposed within the tube to a second deployed state in which the third plurality of anchors and the at least one second anchor extend through at least some of the second plurality of windows into posterior tissue of the native valve.

The annuloplasty device may include a second anterior anchor including a third elongated base, a third plurality of anchors extending from the third elongated base, each anchor of the third plurality of anchors having the first shape, and at least one third anchor extending from the third elongated base and having the second shape, the second anterior anchor designed to transition from a third constrained state fully disposed within the tube to a third deployed state in which the third plurality of anchors and the at least one third anchor extend through at least some of the first plurality of windows into the anterior tissue of the native valve, a second posterior anchor having a fourth elongated base, a fourth plurality of anchors extending from the fourth elongated base, each anchor of the fourth plurality of anchors having the third shape, and at least one fourth anchor extending from the fourth elongated base and having the fourth shape, the fourth posterior anchor designed to transition from a fourth constrained state fully disposed within the tube to a fourth deployed state in which the third plurality of anchors and the at least one fourth anchor extend through at least some of the second plurality of windows into posterior tissue of the native valve.

The first plurality of anchors in the first deployed state and the third plurality of anchors in the third deployed state may be axially aligned with respect to the tube and offset from one another such that the first plurality of anchors in the first deployed state does not interfere with the third plurality of anchors in the third deployed state. The tube may further include a locking window designed to prevent the at least one anterior anchor from transitioning from the first constrained state to the first deployed state. The first elongated base may include a first void biased to reduce in size and a protrusion adjacent to the first void including a first portion and a second portion separated by a second void, and wherein the anterior anchor further may include a pulley designed to move within the first void from a first position designed to cause the first void to expand in size to a second position designed to permit the first void to reduce in size.

When the pulley is in the first position, the first and second portions of the protrusion may be caused to extend into the locking window of the tube and to move apart from one another and, when the pulley is in the second position, the first and second portions of the protrusion may be caused to retract from the locking window and move toward one another permitting the pulley to move with respect to the tube thereby causing the first plurality of anchors to extend through at least some of the plurality of windows and into tissue of the native valve site.

The annuloplasty device may further include a pulley activator in mechanical communication with the pulley and a handle positioned extracorporeally and designed to selectively transition the pulley from the first position to the second position. The at least one first anchor may be substantially linear and is positioned at an end of the elongated base. The annuloplasty device may include a lock having a first engagement designed to engage the first end with the second end and a second engagement designed to selectively disengage the first end and the second end. The tube may include an inner layer having a polymer and an outer layer having a fabric.

Yet another annuloplasty device is provided herein having a tube having an inner lumen, a plurality of windows, and a locking window, the tube designed to form a ring shape upon delivery to a native valve site of a patient, at least one anchor including an elongated base, a plurality of anchors extending from the elongated base, a first void biased to reduce in size, and a protrusion adjacent to the first void and including a first portion and a second portion separated by a second void, and a pulley designed to move within the first void from a first position designed to cause the first void to expand in size to a second position designed to permit the first void to reduce in size, wherein, when the pulley is in the first position, the first and second portions of the protrusion are caused to extend into the locking window of the tube and to move apart from one another and, when the pulley is in the second position, the first and second portions of the protrusion are caused to retract from the locking window and move toward one another permitting the pulley to move with respect to the tube thereby causing the plurality of anchors to extend through at least some of the plurality of windows and into tissue of the native valve site.

The base of the protrusion may include an indention designed to receive a portion of the pulley and to resist movement of the pulley from the first position to the second position. Each anchor of the plurality of anchors has a first shape, and the at least one anchor may further include at least one secondary anchor extending from the first elongated base and having a second shape different than the first shape. The at least one secondary anchor may be positioned at an end of the end of at least one anchor. The first shape may be curved and the second shape may be substantially linear.

The annuloplasty device may further include at least one second anchor including a second elongated base, a plurality of second anchors extending from the second elongated base, a third void biased to reduce in size, and a second protrusion adjacent to the third void and include a third portion and a fourth portion separated by a fourth void, and a second pulley designed to move within the third void from a third position designed to cause the third void to expand in size to a fourth position designed to permit the third void to reduce in size.

The tube may further include a second locking window and wherein, when the second pulley is in the third position, the third and fourth portions of the protrusion are caused to extend into the second locking window of the tube and to move apart from one another and, when the pulley is in the fourth position, the third and fourth portions of the protrusion are caused to retract from the second locking window and move toward one another permitting the second pulley to move with respect to the tube thereby causing the plurality of second anchors to extend through at least some of the plurality of windows and into tissue of the native valve site.

When the pulley is in the second position, the at least one anchor may be designed to enter anterior tissue of the native valve site and, when the second pulley is in the fourth position, the at least one second anchor is designed to enter posterior tissue of the native valve site. The tube may further include a first end and a second end, the annuloplasty device may further include a lock having a first engagement designed to engage the first end with the second end and a second engagement designed to selectively disengage the first end and the second end. The tube may include an inner layer including a polymer and an outer layer including a fabric.

The foregoing summary is illustrative only and is not intended to be in any way limiting. In addition to the illustrative aspects, embodiments, and features described above, further aspects, embodiments, and features will become apparent by reference to the following drawings and the detailed description.

5

Figure 3A:
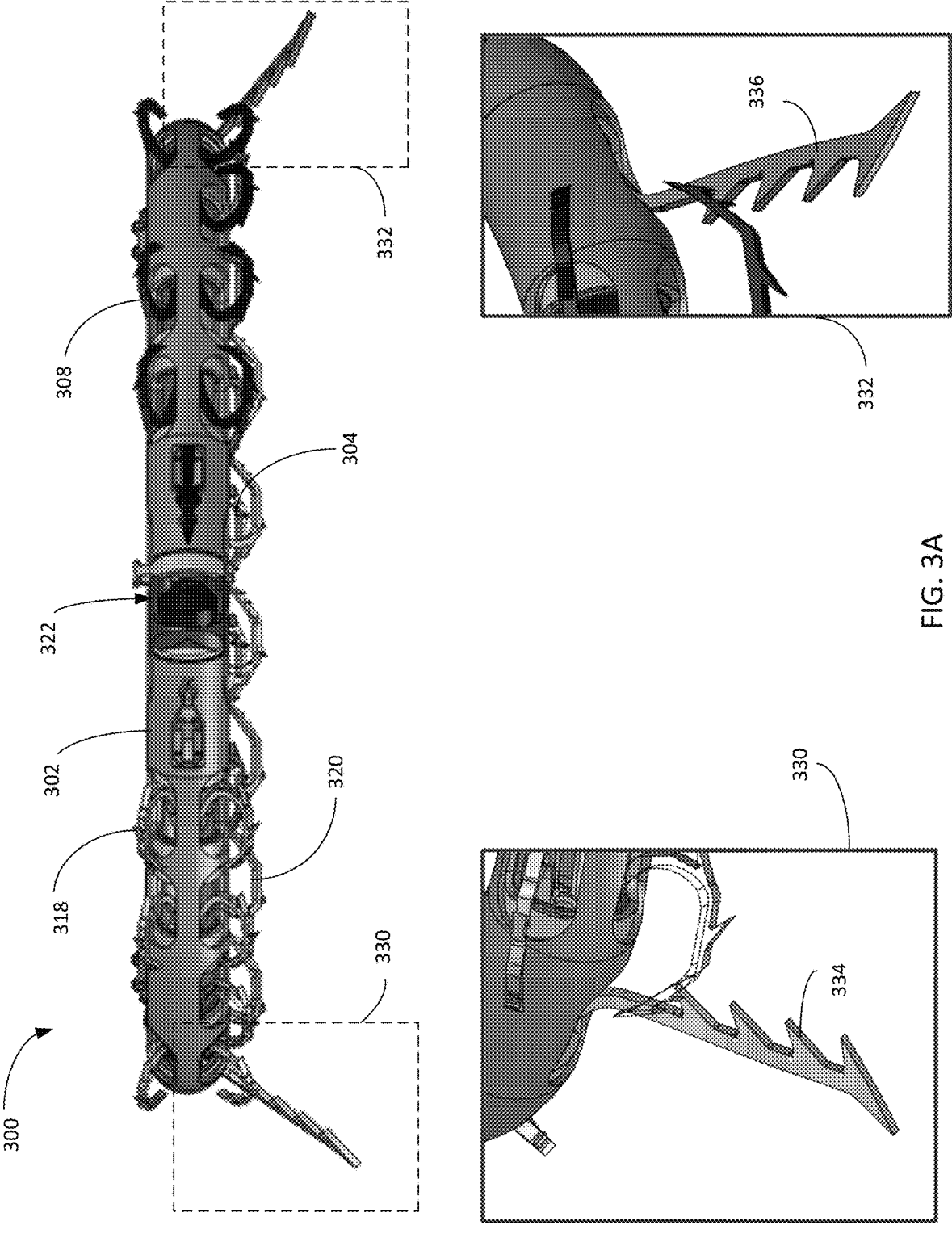
Figure 3B:
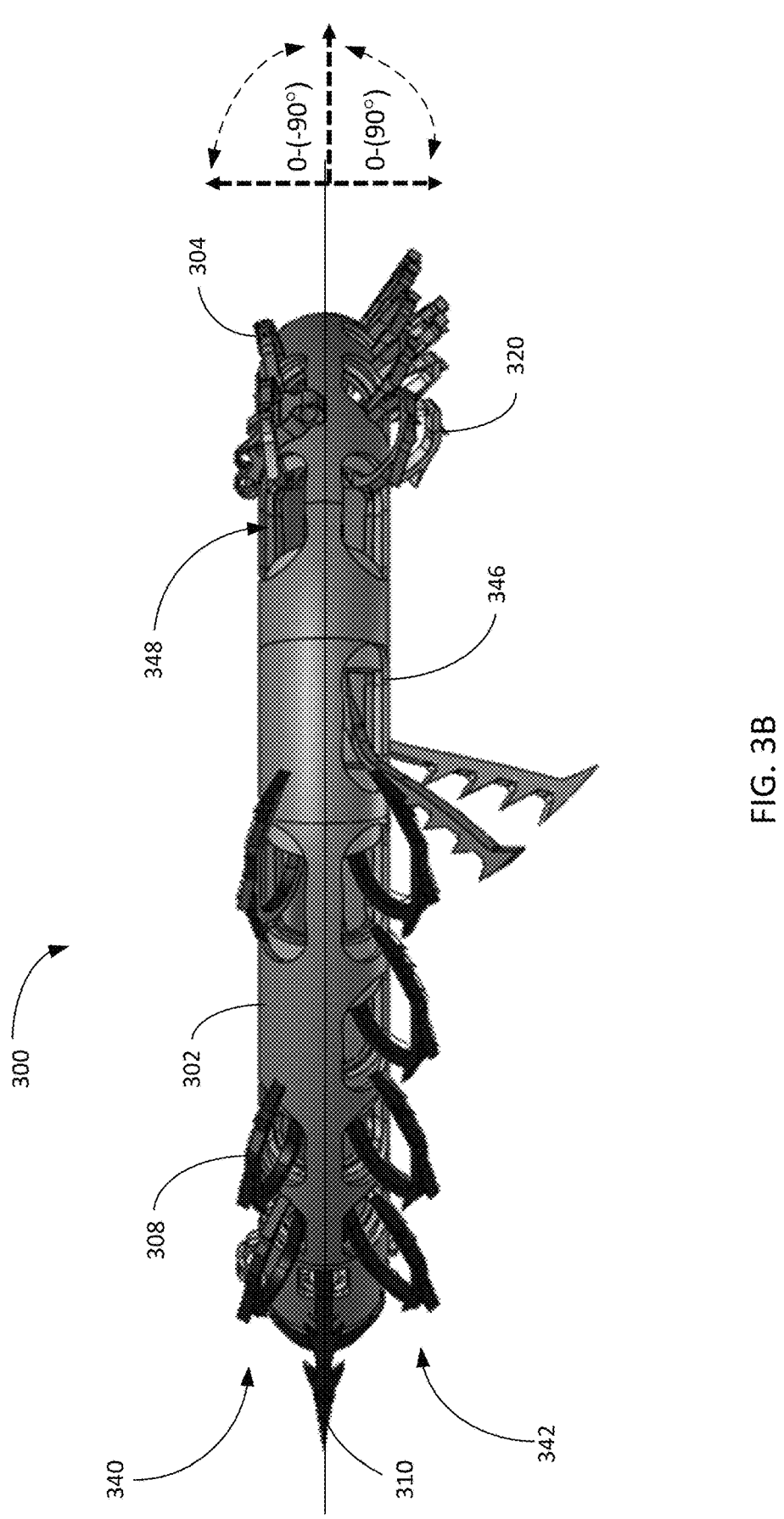
Figure 3C:
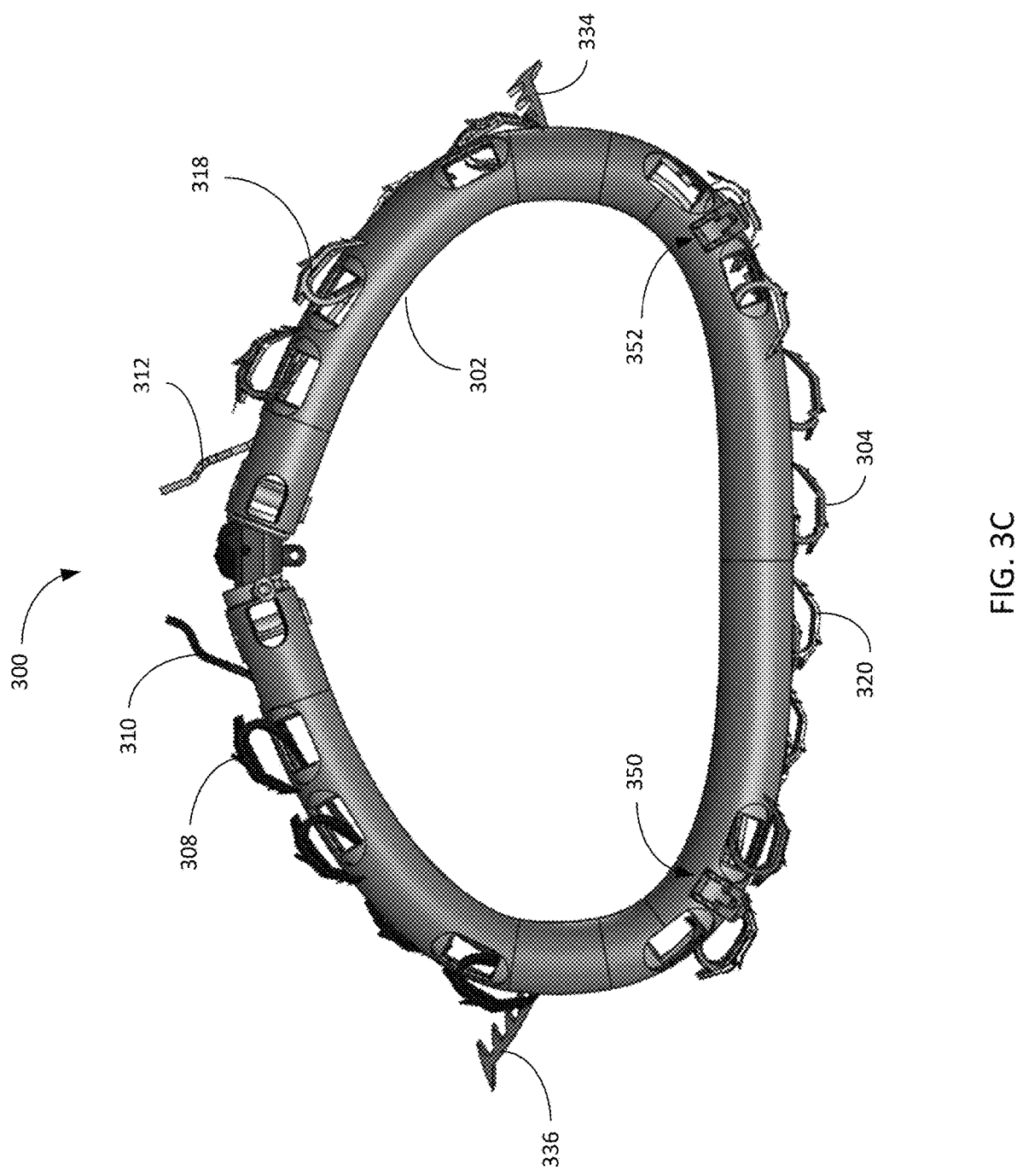

FIGS. 3A-3C illustrate side and top views of an annuloplasty device having anterior and posterior anchors, each with atrial and ventricular anchors.

Figure 4:
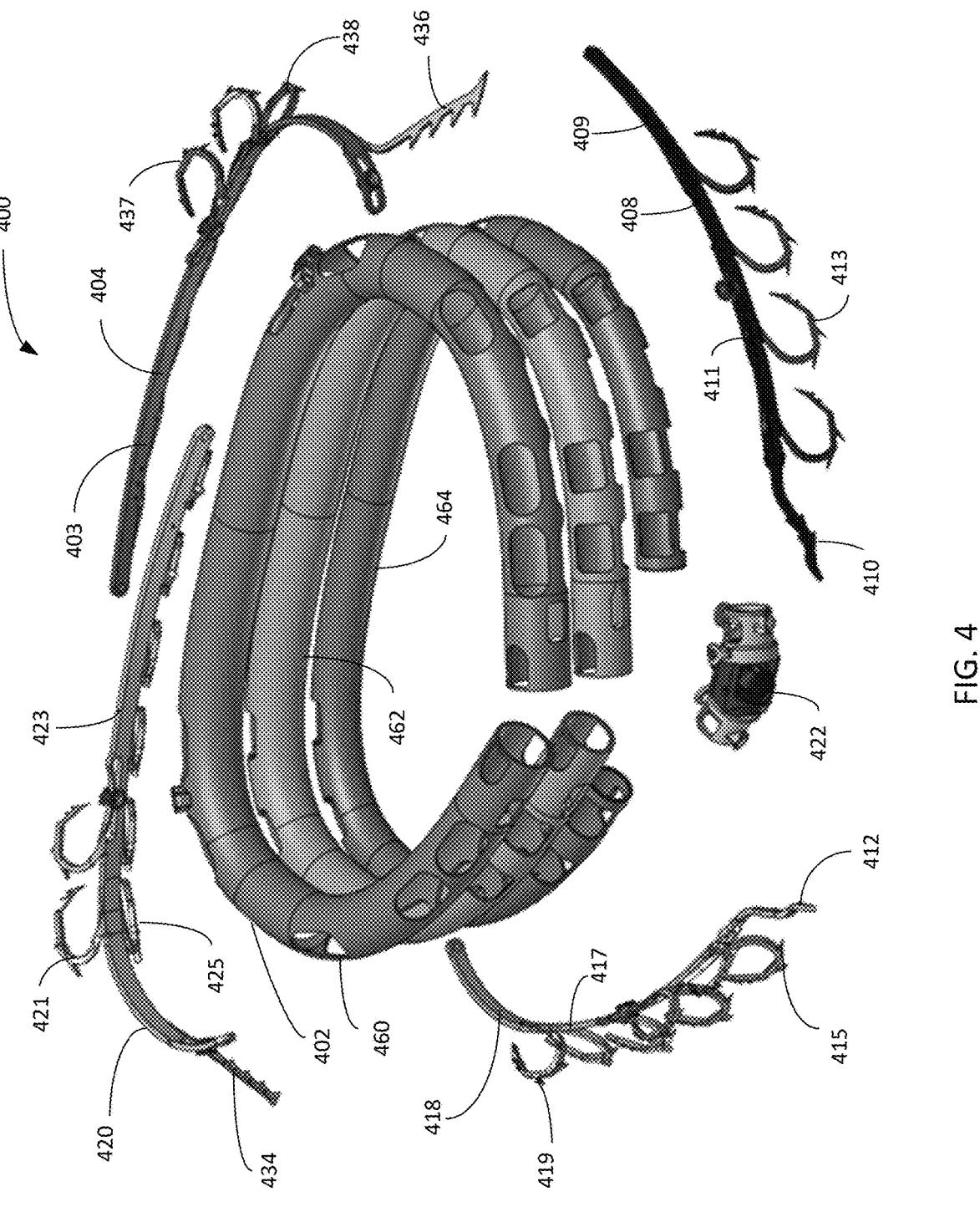

FIG. 4 illustrates an exploded perspective view of an annuloplasty device having two posterior anchors and two anterior anchors.

FIGS. 5A-5E illustrate perspective views and side views of an anterior anchor, pulley, and pulley activator of an annuloplasty device.

Figures 6A, 6B, 6C:
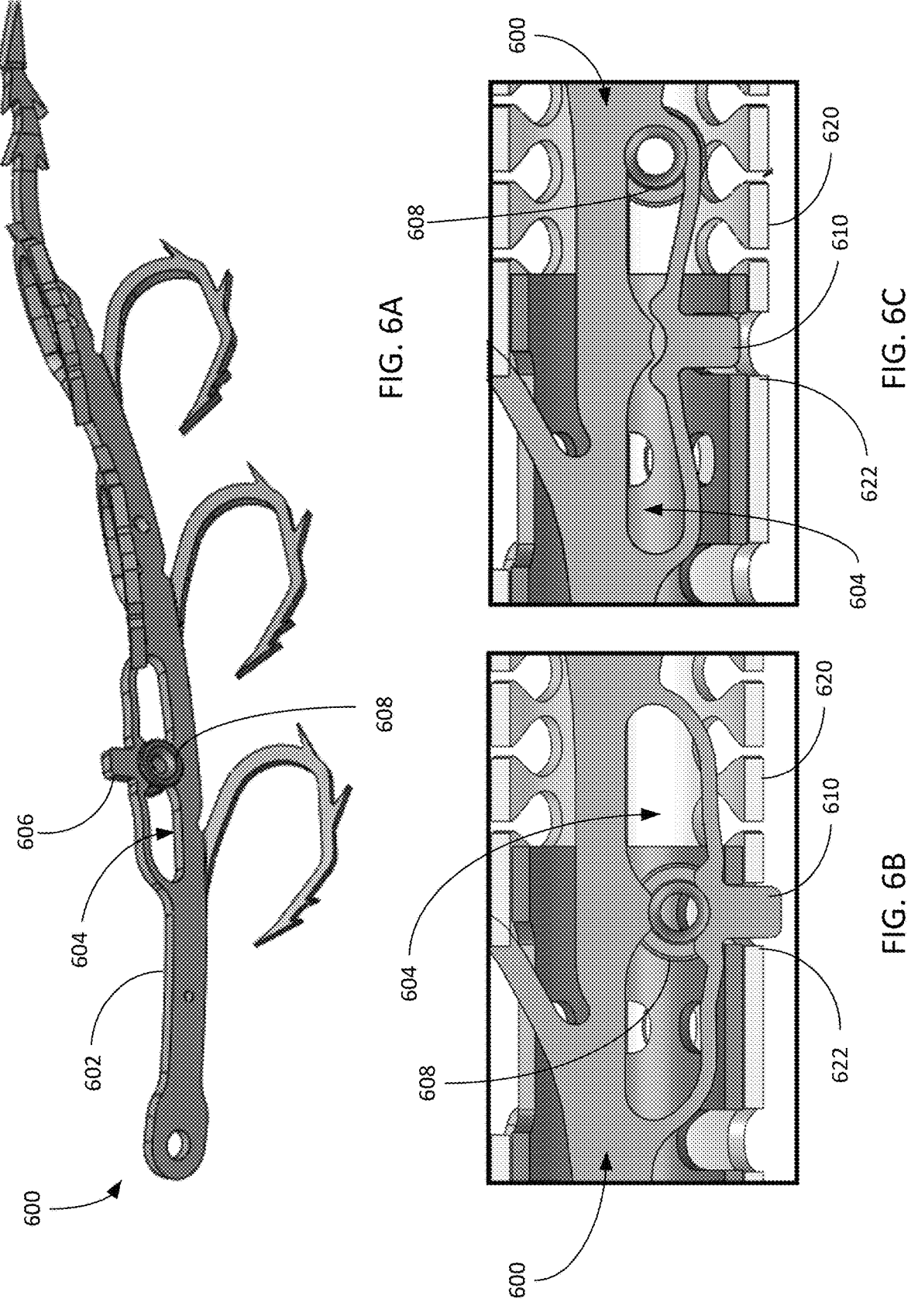

FIGS. 6A-6C illustrate perspective views and side views of a posterior anchor and pulley of an annuloplasty device.

Figures 7A, 7B:
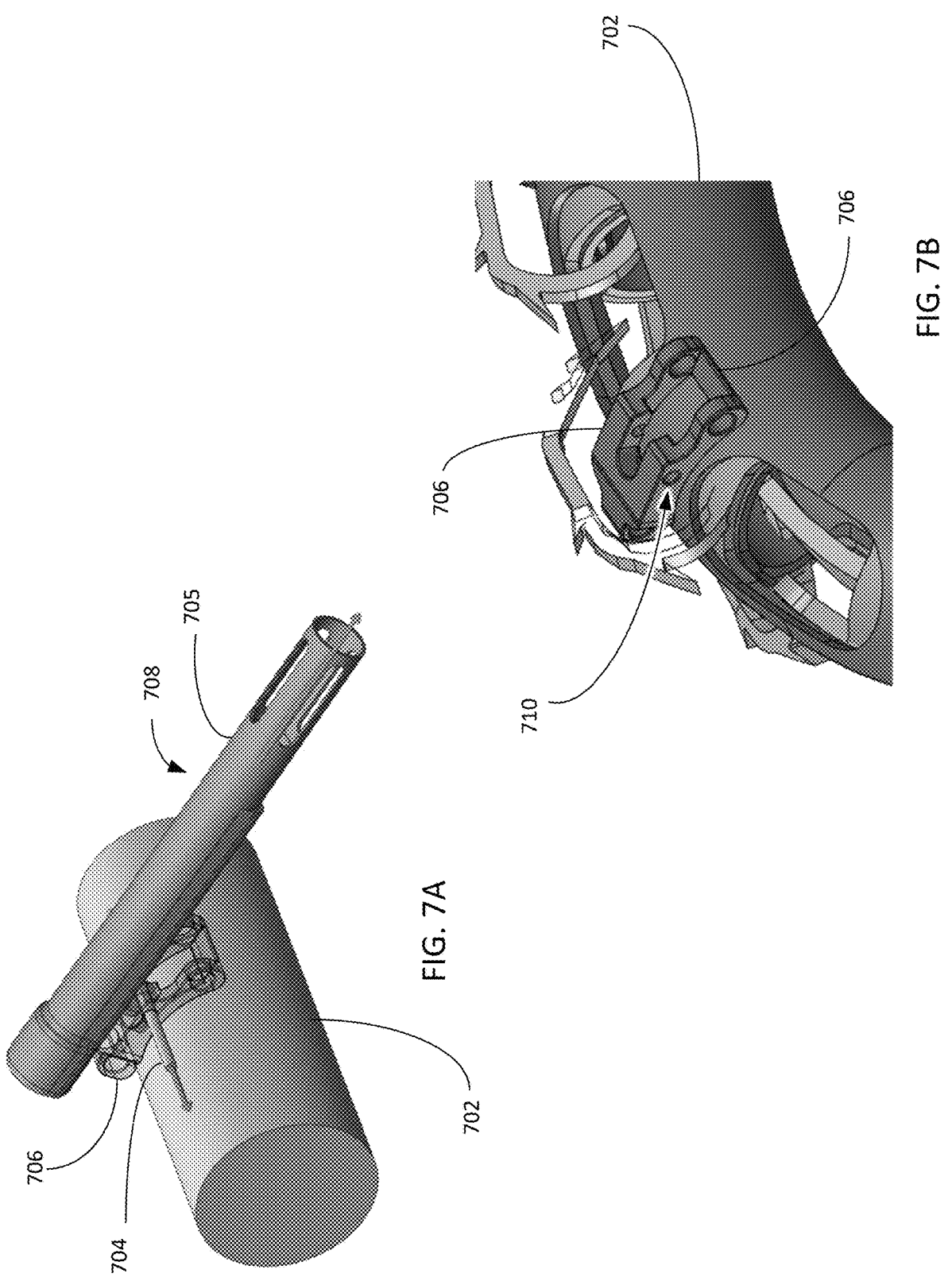
Figure 7C:
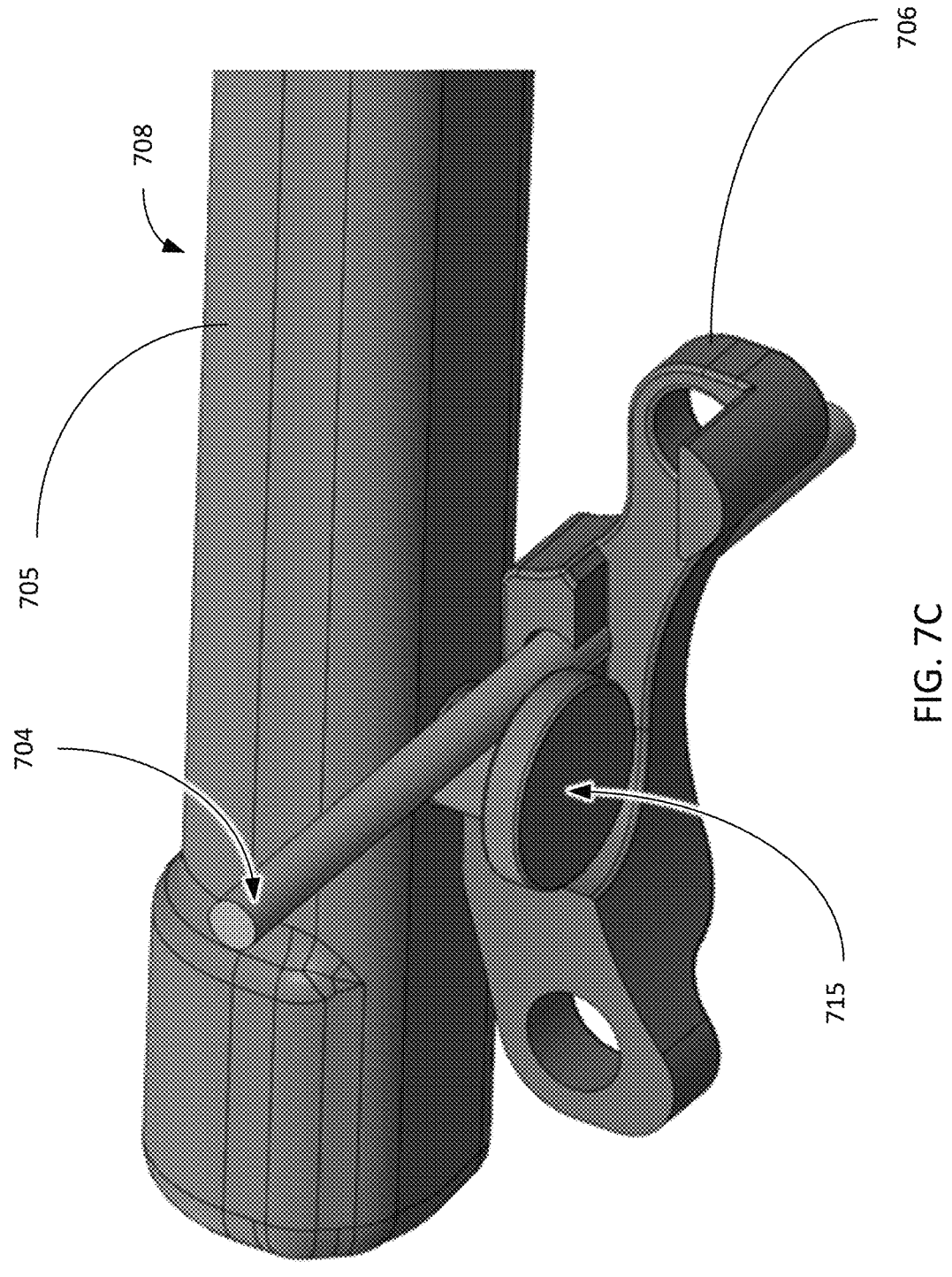

FIGS. 7A-7C illustrate perspective views and cut-away views of a track anchor and a dock of an annuloplasty device.

FIGS. 8A-8G illustrate perspective views deploying track anchors, posterior anchors, and anterior anchors of an annuloplasty device.

The foregoing and other features of the present invention will become apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

DETAILED DESCRIPTION

Provided herein are systems and methods for annuloplasty devices for treating valvular regurgitation. For example, annuloplasty systems may include a catheter system for minimally invasive percutaneous procedures for implanting an annuloplasty device (e.g., an annuloplasty ring) for the treatment of mitral and/or tricuspid regurgitation. The catheter system may include a delivery handle for manipulating the annuloplasty device, which may be positioned in an elongated catheter, delivering the annuloplasty device to a target site of the native valve, aligning the implant with the anatomy to create intimate contact between the annuloplasty device and the anatomy, releasing the annuloplasty device at the target site, and safely retrieving the delivery system.

The annuloplasty device may be used to treat valvular regurgitation and may be formed into a ring shape for implantation at the native valve site (e.g., mitral, tricuspid, etc.). The annuloplasty device may include a tube, which may be a multi-layered tube having multiple windows, one or more posterior anchors and one or more anterior anchors, which each may be selectively transitioned from a constrained positioned within the tube to a deployed positioned extending through the windows and into tissue of the native valve. The annuloplasty device may be delivered to a native valve site in an elongated state and caused to form a ring shape upon reaching the native valve. Track anchors may extend from the distal end of the catheter system and may be used together with the posterior and anterior anchors to reduce an anterior-posterior distance of the native valve to reduce valvular regurgitation.

Figure 1:
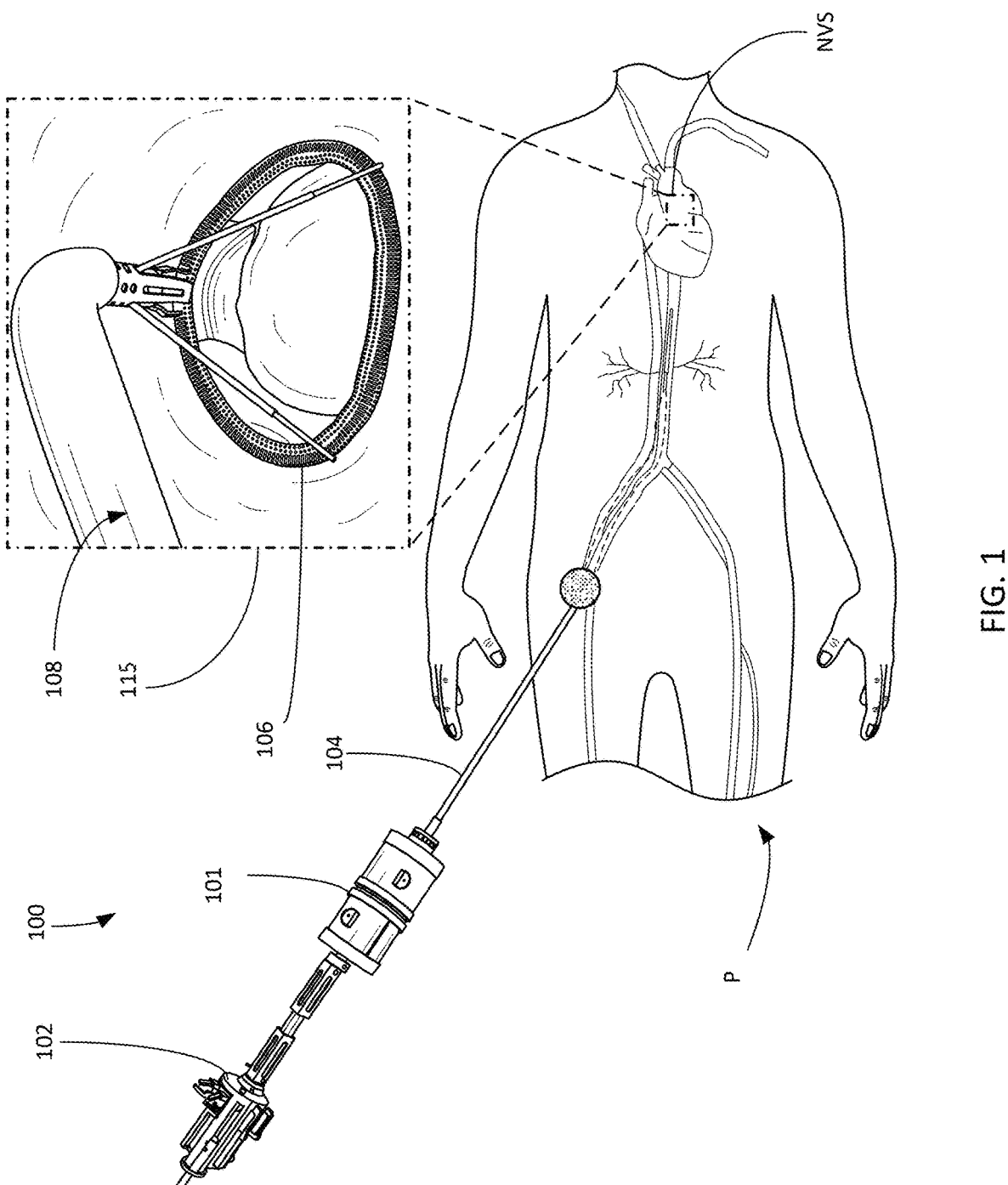
FIG. 1 shows exemplary components of an annuloplasty system for delivering an annuloplasty device for treating valvular regurgitation including a catheter system and an annuloplasty device.

Referring now to FIG. 1, annuloplasty system 100 is illustrated. Annuloplasty system 100 may be used to deliver annuloplasty device 106 to the native valve site NVS (e.g., illustratively the mitral valve) of the patient P. As shown in FIG. 1, annuloplasty system 100 may include catheter system 101 which may include delivery handle 102 and elongated catheter 104, which may extend from delivery handle 102 and may have a distal end 108 that may be inserted into the patient P, for example at the femoral artery. Distal end 108 may be guided to a native valve site at an individual's heart, which may be the mitral valve or any other native valve (e.g., tricuspid valve) experiencing valvular regurgitation. It will be understood by one of ordinary skill in the art that distal end 108 may be introduced to the individual's vasculature at another suitable location (e.g., groin, thigh, stomach, chest, neck, or collar bone, etc.).

Catheter system 101 of annuloplasty system 100 may be similar to the catheter system described in U.S. Pat. No. 10,543,087, the entire contents of which are incorporated herein by reference. Delivery handle 102 may include multiple knobs, actuators, and/or other features for manipulating elongated catheter 104 and/or distal end 108 of the catheter. For example, delivery handle 102 may include one or more knobs and/or actuators for guiding distal end 108 through the patient's vasculature to the native valve site and/or may include multiple knobs and/or actuators for selectively deploying track anchors, posterior anchors, and/or anterior anchors of annuloplasty device 106 to deploy annuloplasty device 106 shown in the close-up view at the native valve site NSV.

Using delivery handle 102, a user of annuloplasty system 100 may deliver annuloplasty device 106 in an elongated state with one end disconnected from another end, and may cause annuloplasty device 106 to form a ring and/or annular shape, as shown in FIG. 1, upon entering the heart. For example, upon entering the left atrium, delivery handle 102 may manipulate annuloplasty device 106 to connect the two ends of annuloplasty ring 106. Knobs and/or actuators in mechanical communication with annuloplasty device 106 and/or distal end 108 may then be manipulated to sequentially release anchors from the posterior and anterior portions of annuloplasty device 106 to close the anterior-posterior gap of the native valve to treat valvular regurgitation.

Figure 2:
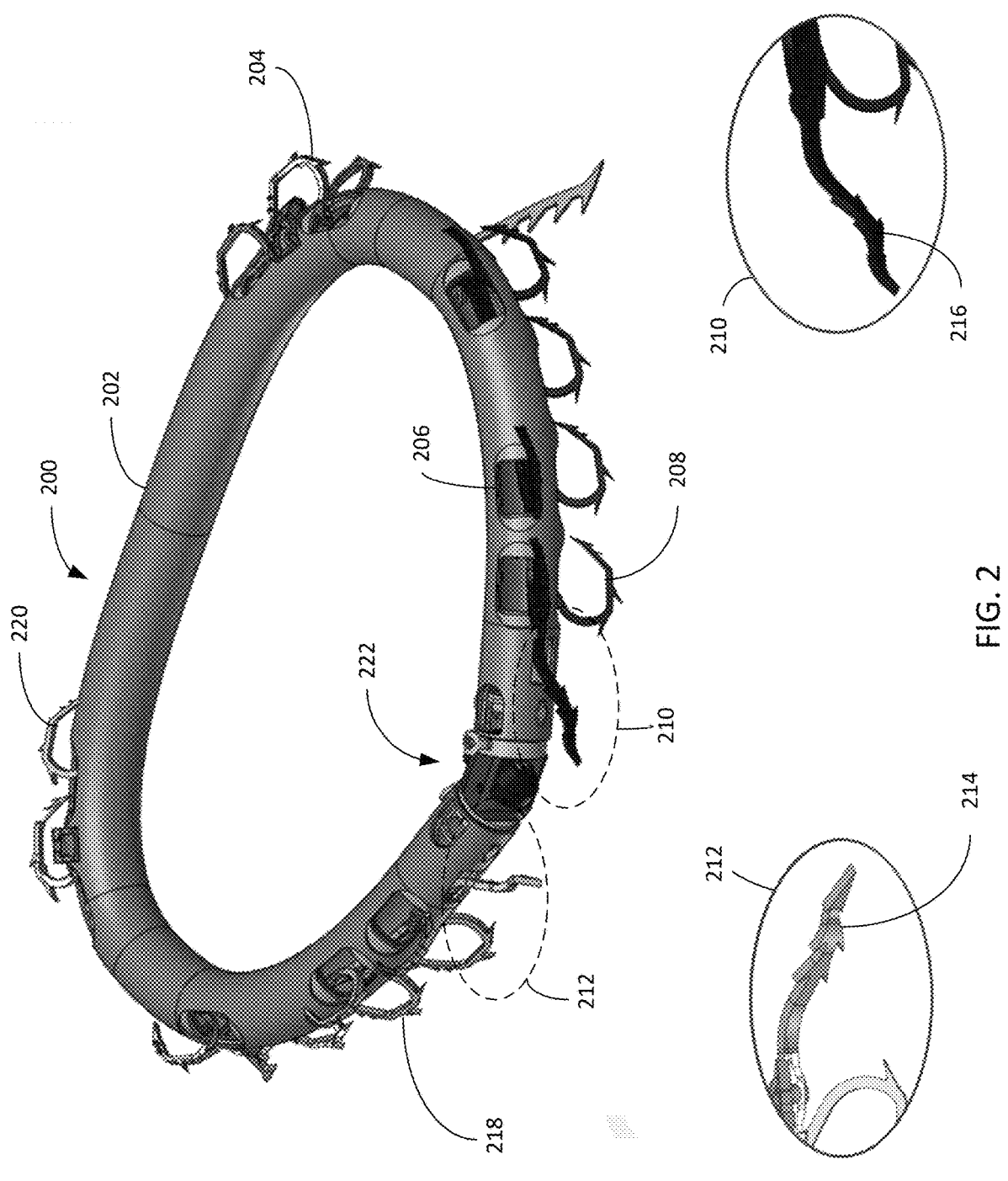
FIG. 2 illustrates a perspective view of an annuloplasty device having anterior and posterior anchors, each with atrial and ventricular anchors.

Referring now to FIG. 2, a perspective view of an annuloplasty device having anterior and posterior anchors, each with atrial and ventricular anchors, is illustrated. As shown in FIG. 2, annuloplasty device 200, which may be the same as or similar to annuloplasty device 106 of FIG. 1, may include tube 202 which may have multiple layers and several windows 206. Windows 206 may extend through an outer layer of tube 202 to an inner lumen of tube 202. Windows 206 may include windows oriented towards an anterior side of annuloplasty device 200, designed to be placed adjacent to anterior tissue of a native valve, as well as a posterior side of annuloplasty device 200, designed to be placed adjacent to posterior tissue of a native valve. Tube 202 may be connected at either end via closure 222 which may include a closing engagement for securing both ends of tube 202 and a release engagement for disengaging each end of tube 202.

Annuloplasty device 200 may include one or more anterior anchors for extending to anterior tissue of a native valve and one or more posterior anchors for extending into posterior tissue to secure annuloplasty device 200 to the anterior and posterior tissue. For example, annuloplasty device 200 may include anterior anchor 220 and anterior anchor 204, which may be transitioned from a constrained state inside of the inner lumen of tube 202 to a deployed state with anchors extending through at least some of windows 206 of tube 202 into anterior tissue of the native valve.

Annuloplasty device 200 may further include posterior anchors 208 and 218, which may be transitioned from a constrained state inside of the inner lumen of tube 202 to a deployed state with anchors extending through at least some of windows 206 of tube 202 into posterior tissue of the native valve. As shown in view 210, locking anchor 216 of posterior anchor 208 may extend towards posterior anchor 218 and similarly, as shown in view 212, anchor 214 of posterior anchor 218 may extend towards posterior anchor 208. Locking anchors 214 and 216 may be serrated and may be designed to secure the ends of annuloplasty device 200 into the tissue of native valve.

Each of anterior anchors 204 and 220 and posterior anchors 208 and 218 may include two rows of curved anchor portions, with one row for insertion into ventricular tissue and another row for insertion into atrial tissue. Each of anterior anchors 204 and 220 and posterior anchors 208 and 218 may further include a non-curved anchor, a linear anchor, and/or an anchor with a shape different than the curved anchors. Each of anterior anchors 204 and 220 and posterior anchors 208 and 218 may be serrated and/or have barbs or hooks for piercing and securing such anchors to tissue of the native valve.

Referring now to FIGS. 3A-3C, side and top views of an annuloplasty device having anterior and posterior anchors, each with atrial and ventricular anchors, are depicted. Annuloplasty device 300, which may be the same as or similar to annuloplasty device 200 of FIG. 2, may include tube 302 as well as anterior anchors 320 and 304 and posterior anchors 318 and 308. Anterior anchors 320 and 304 and posterior anchors 318 and 308 may extend through windows of tube 302 in their deployed positions. Each end of tube 302 may be secured together using closure 322.

As shown in views 330 and 332 of FIG. 3A, anterior anchor 320 may include anchor 334 and anterior anchor 304 may include anchor 336 which each may have a generally linear, straight, and/or non-curved shape. Commissure anchors 334 and 336 may have one side that is serrated for engaging tissue of the native valve. Commissure anchors 334 and 336 may positioned along annuloplasty device 300 such that, when annuloplasty device is delivered to the native valve site (e.g., the mitral valve), anchors 334 and 336 are oriented to be inserted into and/or engage commissures of the native valve. In one example, anchors 334 and 336, despite extending from anterior anchor 320 and anterior anchor 304, respectively, may be positioned adjacent to and may extend into and engage posterior tissue of the native valve site. In this configuration, anchors 334 and 336 may work together with anchors of anterior anchor 320 and anterior anchor 304 positioned to engage anterior tissue of the native valve site to reduce the anterior-posterior distance and maintain (e.g., lock) the reduced anterior-posterior distance.

Referring now to FIG. 3B, a side view of annuloplasty ring 300 is illustrated. As shown in FIG. 3B, tube 302 may include ventricular windows 346 and atrial windows 348. Ventricular windows may be oriented towards a ventricular side of annuloplasty device 300 such that anchors (e.g., anchors 340) extending through ventricular windows 346 may be oriented to extend into ventricular tissue of the native valve and anchors (e.g., anchors 342) extending through atrial windows 348 may be positioned to extend through atrial tissue of the native valve.

Posterior anchor 308 may include atrial anchors extending from an annuloplasty device 300 at an angle of 0 to −45 degree from the centerline illustrated in FIG. 3B. In one example, atrial anchors of posterior anchor 308 may be positioned at an angle or −20 degrees from the centerline annuloplasty device 300. Posterior anchor 308 may further include ventricular anchors extending from a centerline of annuloplasty device 300 at an angle of 0 to 90 degrees. For example, the ventricular anchors of posterior anchor 308 may extend from the centerline of the annuloplasty device

300 at an angle of 45 degrees. Locking anchor 310 of posterior anchor 308 may extent from angle of 0 degrees from the centerline of annuloplasty device 300.

Atrial anchors of anterior anchor 304 may extend from centerline of annuloplasty device 300 from an angle between 0 and −45 degrees. For example, atrial anchors of anterior anchor 304 may extend from the centerline of annuloplasty device 300 at an angle of −20 degrees. Ventricular anchors of anterior anchor 304 and anterior anchor 320 may extend from the centerline of the annuloplasty device at an angle of 0 to 90 degrees. Ventricular anchors of anterior anchors 304 and 320 may be axially aligned with respect to the tube, may be offset from one another, and/or may have a difference in angle from the centerline of at least 5 degrees to avoid interfering with one another. For example, ventricular anchors or anterior anchor 304 may extend at 35 degrees from the centerline and ventricular anchors of anterior anchor 320 may extend at 55 degrees from the centerline of annuloplasty device 300.

Referring now to FIG. 3C, a top-down view of annuloplasty ring 300 is illustrated. As shown in FIG. 3C, anterior anchor 304 may include commissure anchor 336 and anterior anchor 320 include commissure anchor 334 may extend out of anterior windows of tube 302. Additionally, posterior anchor 308 including locking anchor 310 and posterior anchor 318 including locking anchor 312 may extend out posterior windows of tube 202. Docks 350 and 352 may be positioned on top the anterior side of tube 302 and may be designed to connect to a track anchor system of the catheter system, which may be used for aligning annuloplasty device 300 with the native valve.

Referring now to FIG. 4, an exploded perspective view of an annuloplasty device having two posterior anchors and two anterior anchors is illustrated. Annuloplasty device 400 may be the same as or similar to annuloplasty device 300 of FIG. 3. As shown in FIG. 4, tube 402 may include multiple layers such as outer tube 460, intermediate tube 462, and inner tube 464. Outer tube 460 may be a polyester tube and/or cover for example and/or may encourage tissue ingrowth. Intermediate tube 462 may be a hollow ring tube and may form a ring shape. Inner tube 464 may be a laser cut polymer, for example, and/or may reduce friction between anchors and/or anchor components when such components move within tube 402. Each of outer tube 460, intermediate tube 462, and inner tube 464 may include several anterior and posterior windows and/or other windows (e.g., locking windows) for selectively deploying the anchors.

Annuloplasty device 400 may include four anchors, two anterior and two posterior. For example, anterior anchor 420 and anterior anchor 404 may be positioned within an interior of an anterior portion of tube 402. Anterior anchor 420 may include elongated base 423 which may be flat in shape and from which atrial anchors 421 and ventricular anchors 425 may extend from as well as commissure anchor 434. Similarly, anterior anchor 404 may include elongated base 403 which may have a similar shape as elongated base 423 and from which atrial anchors and ventricular anchors 438 may extend as well as commissure anchor 436. Atrial anchors 437 and 421 and ventricular anchors 438 and 435 may be curved in shape and may be serrated. In one example, atrial anchor 437, atrial anchor 421, ventricular anchor 438, and/or ventricular anchor 435 may be the same shape. The shape of commissure anchors 434 and 436 may be generally linear, straight, or non-curved. In one example, commissure anchors 434 and 436 may be the same shape.

Commissure anchors 434 and 436, despite extending from anterior anchor 420 and anterior anchor 404, respectively, may be positioned adjacent to and may extend into and engage posterior tissue of the native valve site. In this configuration, anchors 434 and 436 may work together with anchors of anterior anchor 420 and anterior anchor 404 positioned to engage anterior tissue of the native valve site (e.g., atrial anchors 421 and 437 and ventricular anchors 425 and 438) to reduce the anterior-posterior distance and maintain (e.g., lock) the reduced anterior-posterior distance.

Posterior anchors 418 and 408 may be positioned within a posterior portion of tube 402. Interior anchor 408 may include elongated base 409 which may be flat in shape and from which atrial anchors 411 and ventricular anchors 413 may extend from along with locking anchor 410. Similarly, interior anchor 418 may include elongated base 417 having a flat shape and atrial anchors 419 and ventricular anchors as well as locking anchor 412 that extend therefrom. Atrial anchors 419 and 411 and ventricular anchors 415 and 413 may have a curved shape with a serrated edge. The shape of locking anchors 412 and 410 may be generally linear, straight, or non-curved. In one example, atrial anchor 419, atrial anchor 411, ventricular anchor 415, and/or ventricular anchor 413 may have the same shape. Alternatively, or additionally, locking anchor 412 and locking anchor 410 may have the same shape.

Closure 422 may be positioned into ends of tube 402 and may be secured to each end of tube 402. For example, closure 422 may be the same as or similar to the closure device described in U.S. Pat. No. 11,576,779, the entire contents of which are incorporated herein by reference. Closure 422 may be lock having a primary engagement for engaging each end of the annuloplasty device to form an annular shape and a secondary engagement, different from the primary engagement selectively disengage ends of the annuloplasty device. For example, the primary engagement may be a snapping engagement and the secondary engagement may be formed from pin that may be removed to separate ends of the annuloplasty device. While three layers of tube 402, two posterior anchors, and two anterior anchors and illustrated, it will be one understood of one of ordinary skill in the art that any number of layers and/or anchors may be used.

Figures 5A, 5B, 5C:
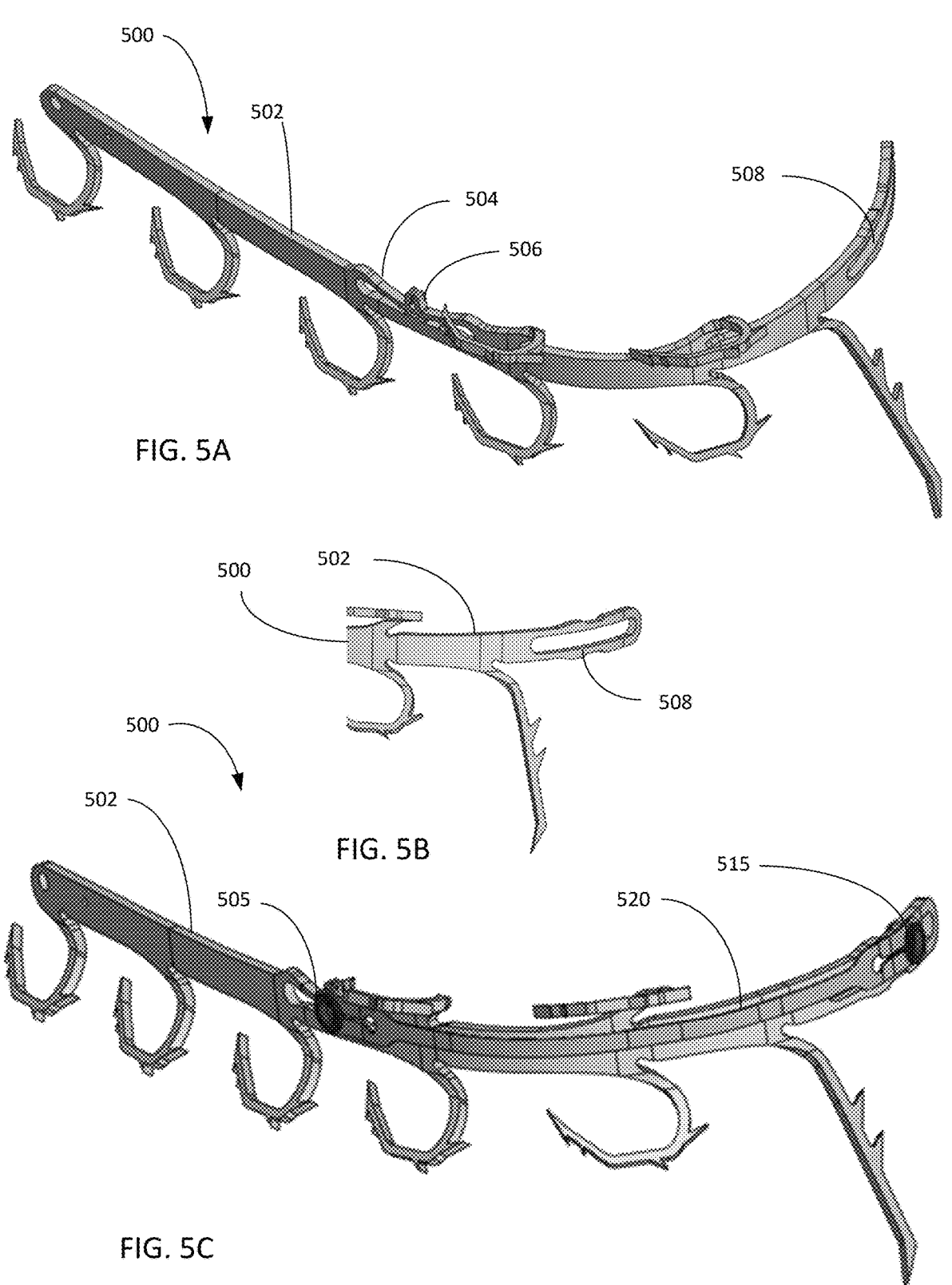

Referring now to FIG. 5A-5E perspective views and side views of an anterior anchor, pulley, and pulley activator of an annuloplasty device are illustrated. As shown in FIGS. 5A and 5B, anterior anchor 500 may include elongated base 502, which may be a flat and/or curved structure having several ventricular anchors (e.g., five) and atrial anchors (e.g., two) extending from elongated base 502. Elongated base 502 may include void 504 and void 508. Void 504 may be biased to reduce in size. Protrusion 506 may be positioned adjacent to void 504 and may move as void 504 increases and decreases in size.

Referring now to FIG. 5C, anterior anchor 500 may include pulley 505 positioned within void 504 and pulley 515 positioned within void 508. Pulley 505 and pulley 515 may be circular structures that move within and are guided by voids 504 and 508. Pulley 505 and pulley 515 may be connected by pulley activator 520, which may be in mechanical communication with each of pulley 505 and pulley 515 as with as the delivery handle positioned extracorporeally and may cause pulley 505 and pulley 515 to move together. Pulley 515 and/or pulley 505 may be engaged with a cable (e.g., suture, wire, cable, etc.) that may extend through the elongated catheter to the delivery handle and may be moved by the delivery handle to move pulleys 505 and 515 within voids 504 and 508 to transition anterior anchor 500 from a constrained position to a deployed position.

Figures 5D, 5E:
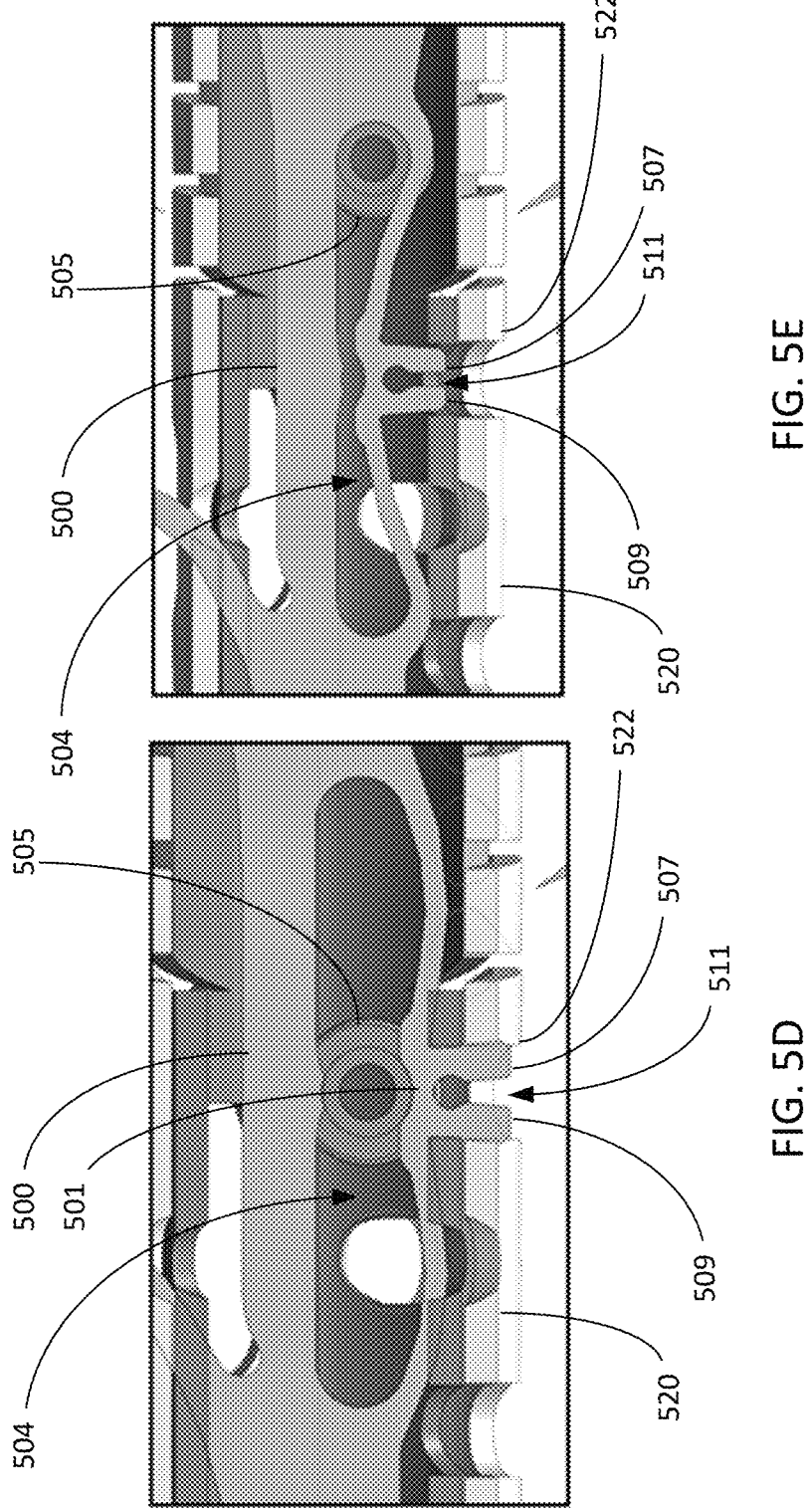

Referring now to FIGS. 5D and 5E, void 504 is illustrated with a reduced size in FIG. 5E as compared to FIG. 5D. As shown in FIG. 5D, pulley may be positioned in the middle of void 504 to cause void 504 to open, thereby extending protrusions 509 and 507 outward (e.g., away from void 504. Protrusions 509 and 507 may be adjacent to void 504 and may include void 511 separating protrusion 509 and 507. Void 504 may include one or more indention (e.g., indentation 501) such that pulley rests in indentation 501. When pulley 505 is in indentation 501 void 504 is caused to open thereby causing protrusions 507 and 509 to extend into locking window 522 of tube 520. With protrusions 507 and 509 in locking window 522, anterior anchor 500 may be prevented from moving with respect to tube 520.

As shown in FIG. 5E, to move anterior anchor 500 with respect to tube 520, the delivery handle may be actuated or otherwise manipulated to advance pulley 505 to the left or the right to permit void 504 to reduce in size. As void 504 reduces in size, protrusions 509 and 507 may be retracted upward and void 511 may be reduced in size as protrusions 509 and 507 are retracted upward, causing protrusions 507 and 509 to exit locking window 522. With protrusions 507 and 509 removed from locking window, anterior anchor 500 may move with respect to tube 520.

Referring now to FIGS. 6A-6C, perspective views and side views of a posterior anchor and pulley of an annuloplasty device are illustrated. Posterior anchor 600 may include elongated base 602 which may be a flat and/or curved structure from which multiple ventricular anchors (e.g. three) and multiple atrial anchors (e.g., two) extend as well as a locking anchor. Elongated base 602 may further include void 604 which may be biased to reduce in size and may guide pulley 608 within void 604. Protrusion 610 may be positioned adjacent to void 604 and may extend away from void 604 when void 604 increases in size and retract toward void 604 when void is reduced in size.

When pulley 608 is positioned in the middle of void 604, pulley 608 may cause void 604 to expand, causing protrusion 610 to extend into locking window 622 of tube 620. As shown in FIGS. 6B and 6C, the delivery handle may connect to pulley 608 (e.g., via a cable, suture, wire, etc.) and may cause pulley 608 to move to right or the left to cause void 604 to reduce in size. When void 604 reduces in size, protrusion 610 is retracted towards void 604 and thus exits locking window 610, permitting posterior anchor 600 to move with respect to tube 620.

Referring now to FIGS. 7A-7C, perspective views and cut-away views of a track anchor and a dock of an annuloplasty device are illustrated. As shown in FIG. 7A, tube 702 of a annuloplasty device which may be the same as or similar to annuloplasty ring 300 of FIG. 3A, may include dock 706 which may connect to track anchor system 708 and specifically sleeve 705 of track anchor system 708, which may deliver track anchors for aligning the annuloplasty device with the native valve site. Release cable 704 may be inserted into dock 706 and through a portion of track anchor system 708 to secure track anchor system 708 to dock 706.

FIG. 7B illustrates dock 706 connected to an outer surface of tube 705. Dock 706 may include through holes 710 for receiving a release cable to secure the track anchor system to dock 706. Release cable may be connected to the delivery handle and may be manipulated by the delivery handle. In another example, multiple release cables may be used. Referring now to FIG. 7C, a cut-away perspective view of dock 706 is illustrated showing protrusion 715 which may have disk shape offset from sleeve 705 of anchor track system 708 such that release cable 704 may be inserted between protrusion 715 and sleeve 705 to prevent protrusion 715 from being released from dock 706. When release able 704 is removed from dock 706, sleeve 705 may be removed from dock 706.

Figure 8A:
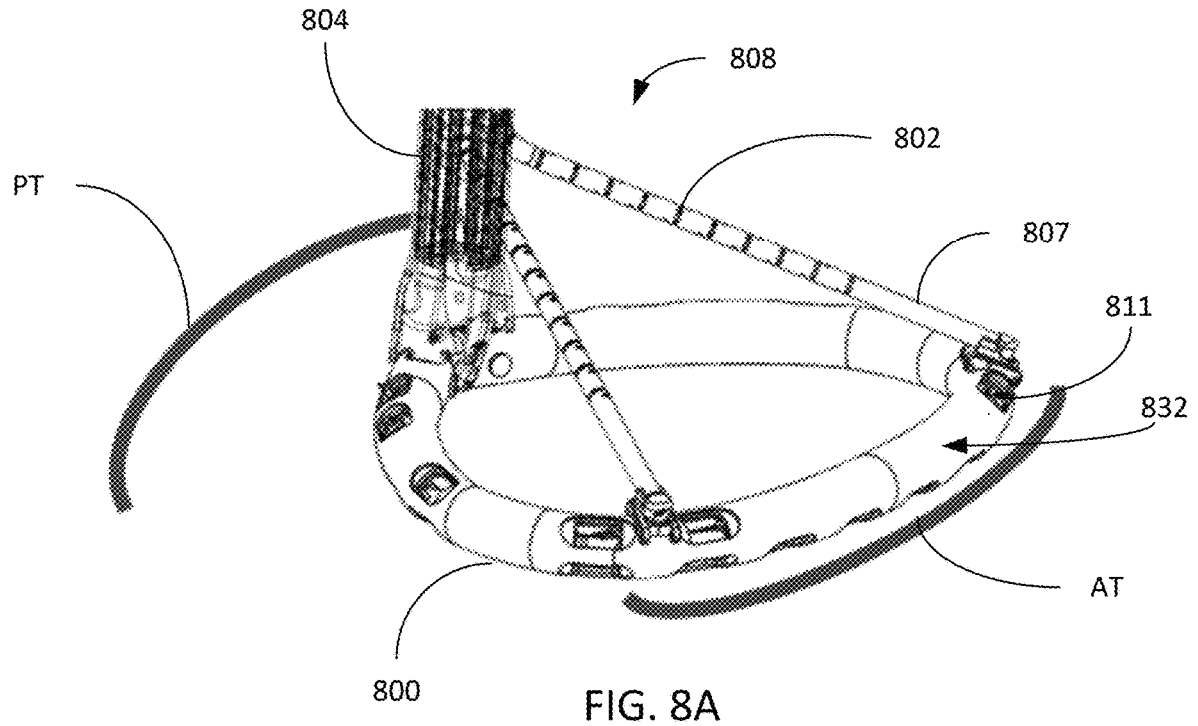

Referring now to FIGS. 8A-8G, perspective views of an annuloplasty device deploying track anchors, posterior anchors, and anterior anchors for reducing an anterior-posterior distance of a native valve are illustrated. As shown in FIG. 8A, annuloplasty device 800, which may be the same as or similar to annuloplasty device 300 of FIG. 3A, may be delivered to a native valve site (e.g, mitral valve site or tricuspid valve site), and anterior side 832 of annuloplasty device 800 having anterior anchors for engaging anterior tissue of the native valve site (e.g., a portion of the native valve from which anterior leaflets extend) may be aligned with the anterior tissue via distal end 804 of the delivery catheter and track anchor system 808. Track anchor system 808 may include two of such hollow cannulas (e.g., cannulas 802) that may be connected to sleeves (e.g. sleeves 807), which may be releasably connected to the tube of annuloplasty device 800 at docks 811, as shown in FIGS. 7A-7C. In one example, track anchor system 808 may be similar to the track anchor system described in more detail in U.S. Pat. No. 11,857,418, the entire contents of which are incorporated herein by reference.

Figure 8B:
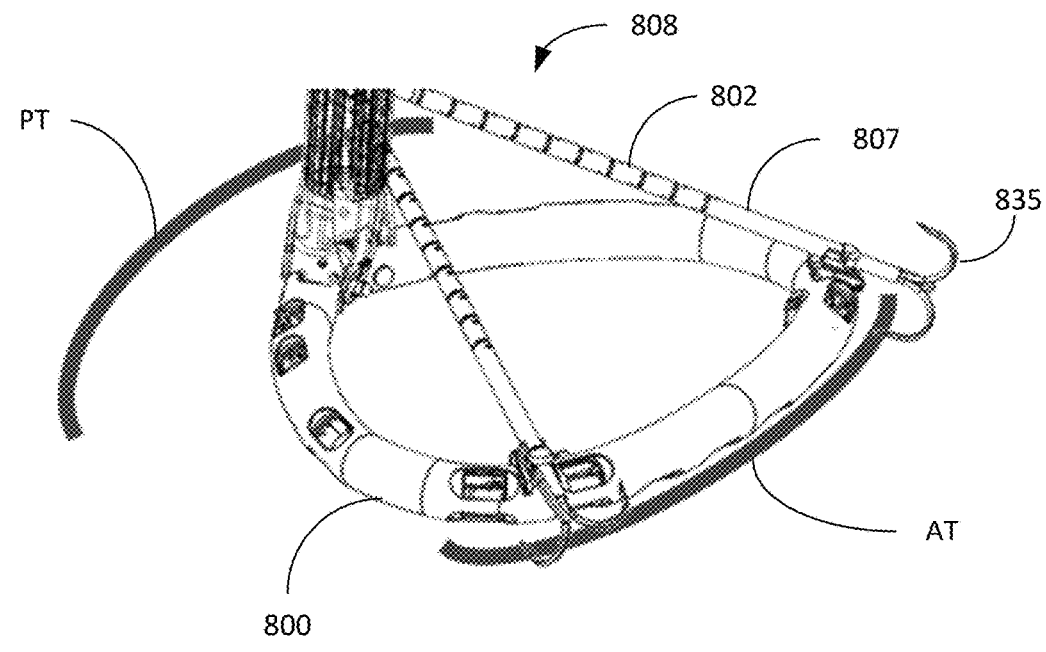

Anchor track system 808, which may include cannulas 802 from distal end 804 of the delivery catheter and connect sleeves (e.g. sleeve 807) which may connect to the docks (e.g., docks 811) of annuloplasty device 800 may be used to align annuloplasty device 800 with the native valve site, and specifically align the anterior portion 832 of annuloplasty device 800 with anterior tissue AT of the native valve site. Once anterior portion 832 is adjacent to anterior tissue AT of the native valve site, the delivery handle may be manipulated to cause track anchors 835 to traverse track anchor system 808 and exit a distal end of sleeve 807 to insert a portion of track anchors 835 into the native anterior valve tissue, as shown in FIG. 8B. For example, two track anchors, one from each sleeve of track anchor system 808 may extend into tissue of the native heart valve.

Figure 8C:
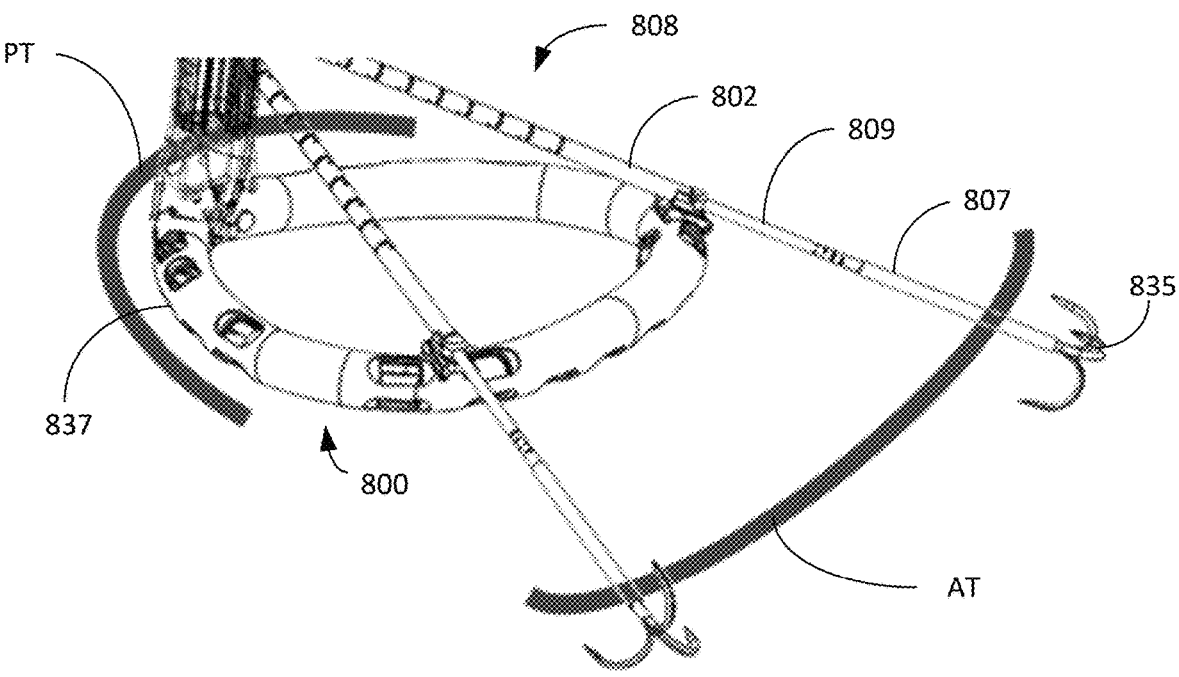
Figure 8D:
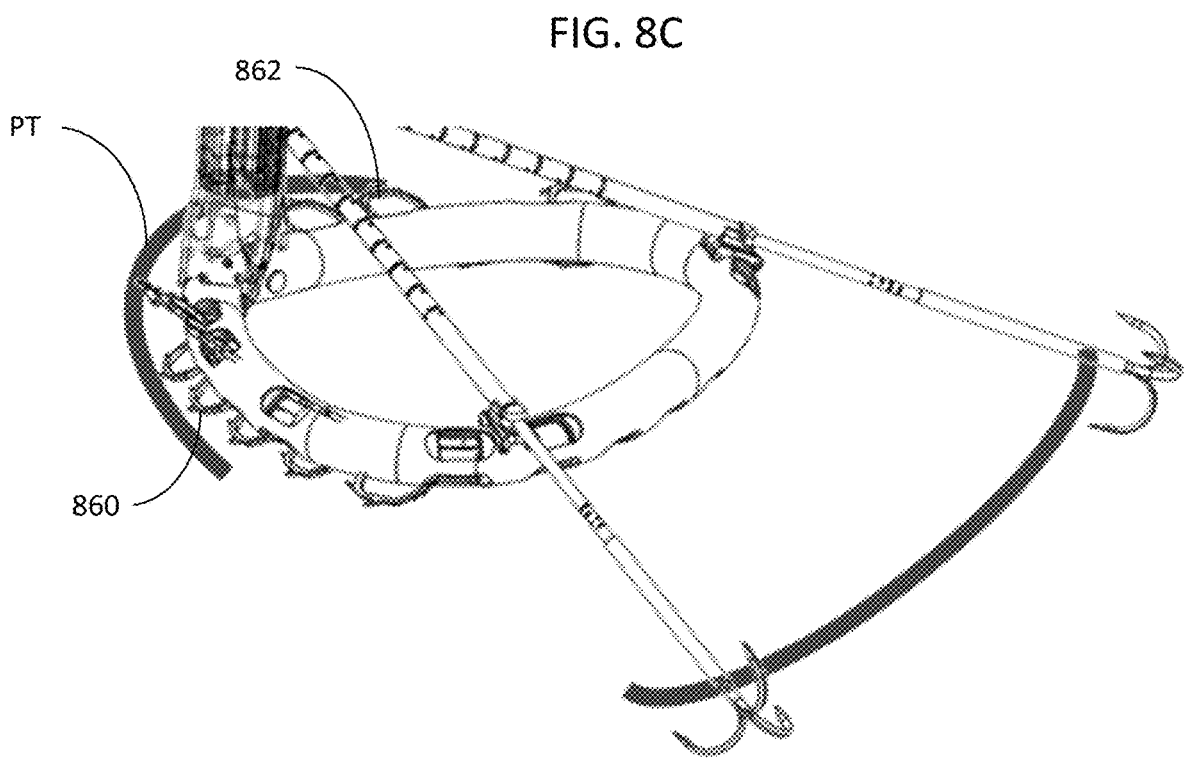

Referring now to FIG. 8C, once track anchors 835 are deployed into anterior tissue AT, distal end 804 may move annuloplasty device 800 to align posterior portion 837 of annuloplasty device 800 with posterior tissue PT. As annuloplasty device 800 is moved away from track anchors 835, cables 809 connected at one end of track anchors 835 may maintain a connection between track anchors 835 and track anchor system 808. Once annuloplasty device 800 is positioned adjacent to posterior tissue PT, posterior anchors 860 and 862 may be deployed into the posterior tissue of the native valve, as shown in FIG. 8D. Posterior anchors may be the same as or similar to posterior anchors 418 and 408 of FIG. 4, for example. Posterior anchors 860 and 862 may be deployed sequentially using separate actuators on the delivery handle or may be deployed at the same time using a single actuator on the delivery handle.

Figure 8E:
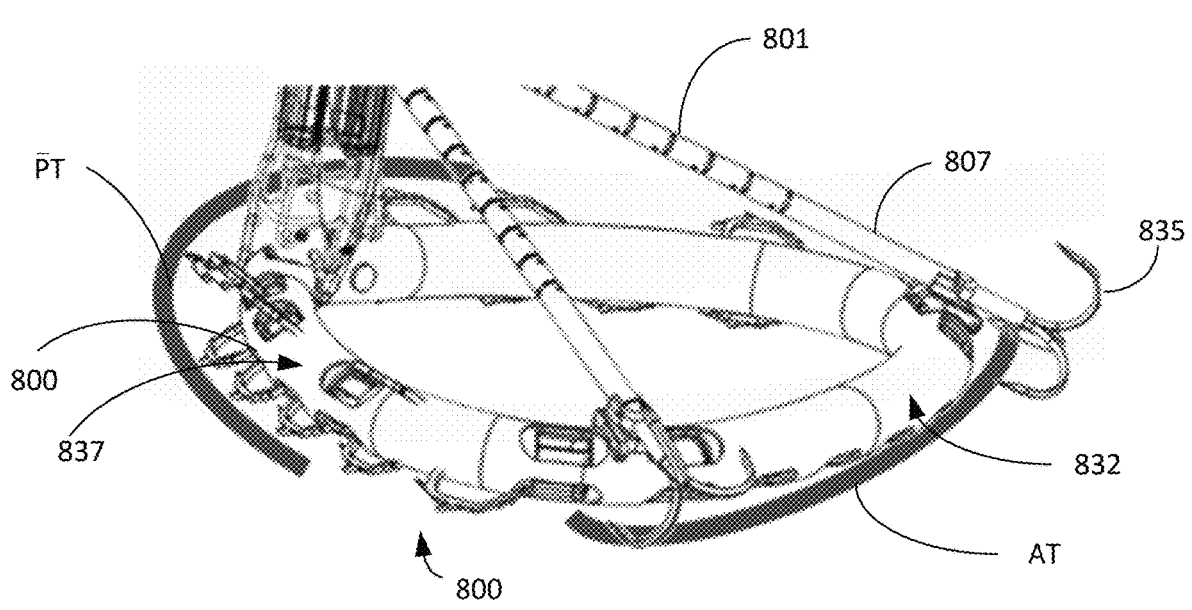
Figure 8F:
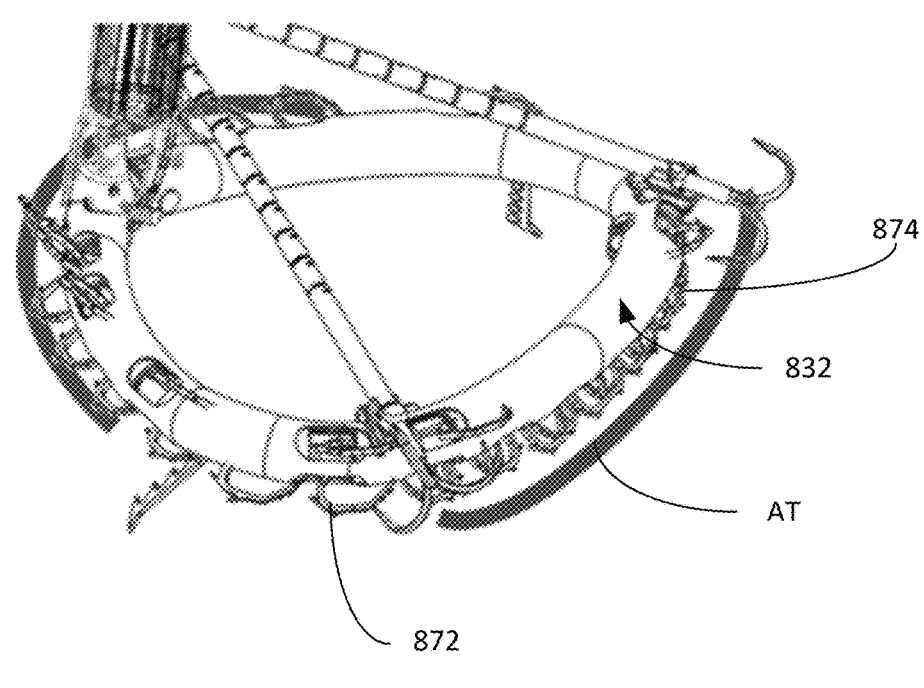

Referring now to FIG. 8E, cable 809 (not shown) may be retracted into cannula 802 to pull annuloplasty device 800 back towards anterior tissue AT to reduce the distance between posterior tissue PT and anterior tissue AT thereby causing posterior portion 837 of annuloplasty device 800 to be adjacent to anterior tissue PT and anterior portion 832 to be adjacent to anterior tissue AT. As shown in FIG. 8F, once anterior portion 832 of annuloplasty device 800 is adjacent anterior tissue AT, anterior anchors 872 and 874 may be deployed and extended into anterior tissue AT to secure anterior portion 832 into anterior tissue AT. Anterior anchors 872 and 874 may be the same as or similar to anterior anchors 420 and 404 of FIG. 4. Anterior anchors 872 and 874 may be deployed sequentially using separate actuators on the delivery handle or may be deployed at the same time using a single actuator on the delivery handle. In one example, anchors 888 and 889 may extend from anterior anchor 872 and anterior anchor 874, respectively, and may be positioned adjacent to and may extend into and engage posterior tissue of the native valve site. In this configuration, anchors 888 and 889 may work together with anchors of anterior anchor 874 and anterior anchor 889 positioned to engage anterior tissue of the native valve site to reduce the anterior-posterior distance and maintain (e.g., lock) the reduced anterior-posterior distance illustrated in FIG. 8F.

Figure 8G:
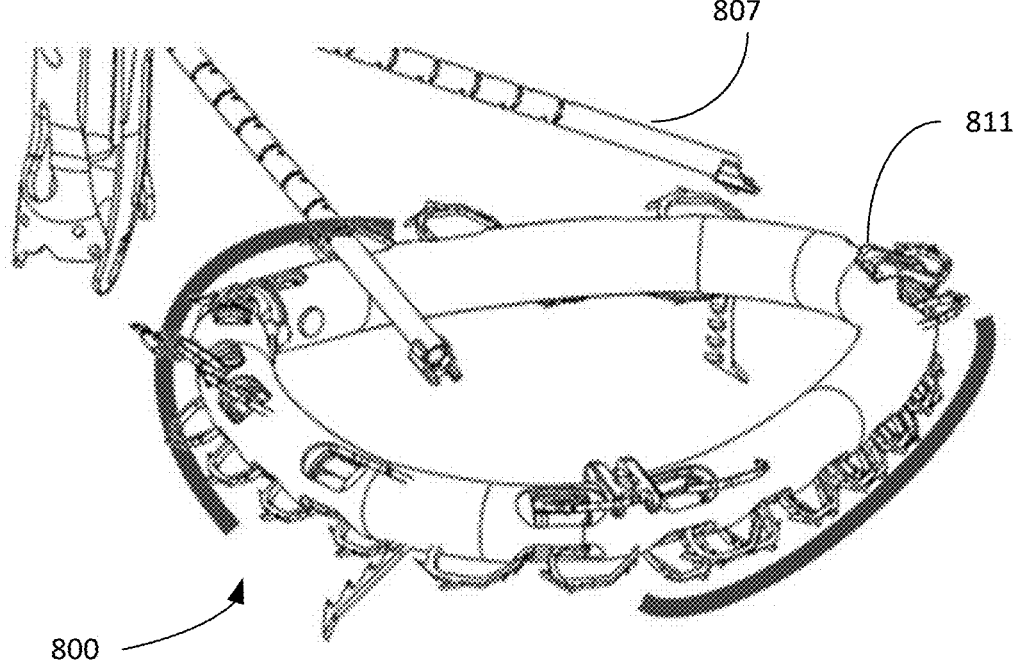

Referring now to FIG. 8G, once posterior and anterior anchors are deployed from annuloplasty device 800, the track anchors may be retracted into sleeve 807 and each sleeve 807 may be disconnected from docks 811 by manipulating the delivery device to remove the release cable, thereby disconnecting annuloplasty device 800 from the distal end of the delivery catheter. Once annuloplasty device 800 is released from the delivery catheter, the delivery catheter may be retracted and removed from the patient, leaving the annuloplasty device implanted at the native valve site.

The foregoing description of illustrative embodiments has been presented for purposes of illustration and of description. It is not intended to be exhaustive or limiting with respect to the precise form disclosed, and modifications and variations are possible in light of the above teachings or may be acquired from practice of the disclosed embodiments. It is intended that the scope of the invention be defined by the claims appended hereto and their equivalents.

What is claimed is:

1. An annuloplasty device comprising:
a tube comprising a first end, a second end, an inner lumen, a first plurality of windows, and a second plurality of windows, the first plurality of windows configured to be orientated toward anterior tissue of a native valve and a second plurality of windows configured to be orientated toward posterior tissue of the native valve when the annuloplasty device is implanted at a native valve site;
at least one anterior anchor comprising a first elongated base, a first plurality of anchors extending from the first elongated base, each anchor of the first plurality of anchors having a first shape, and at least one first anchor extending from the first elongated base and having a second shape different than the first shape, the at least one anterior anchor configured to transition from a first constrained state fully disposed within the tube to a first deployed state in which the first plurality of anchors and the at least one first anchor extend through at least some of the first plurality of windows and the first plurality of anchors extends into the anterior tissue of the native valve; and
at least one posterior anchor comprising a second elongated base and a second plurality of anchors extending from the second elongated base, each anchor of the second plurality of anchors having a third shape, the at least one posterior anchor configured to transition from a second constrained state fully disposed within the tube to a second deployed state in which the second plurality of anchors extend through at least some of the second plurality of windows into posterior tissue of the native valve.

2. The annuloplasty device of claim 1, wherein the at least one posterior anchor further comprises at least one second anchor extending from the second elongated base and having a fourth shape different than the third shape.

3. The annuloplasty device of claim 1, wherein the at least one first anchor extends into posterior tissue of the native valve when the at least one anterior anchor is in the first deployed state.

4. The annuloplasty device of claim 1, wherein the third shape is the same as the first shape.

5. The annuloplasty device of claim 1, further comprising:
   a second anterior anchor comprising a third elongated base, a third plurality of anchors extending from the third elongated base, each anchor of the third plurality of anchors having the first shape, and at least one second anchor extending from the third elongated base and having the second shape, the second anterior anchor configured to transition from a third constrained state fully disposed within the tube to a third deployed state in which the third plurality of anchors and the at least one third anchor extend through at least some of the first plurality of windows and the third plurality of anchors extends into the anterior tissue of the native valve; and
   a second posterior anchor comprising a fourth elongated base, a fourth plurality of anchors extending from the fourth elongated base, each anchor of the fourth plurality of anchors having the third shape, the second posterior anchor configured to transition from a fourth constrained state fully disposed within the tube to a fourth deployed state in which the third plurality of anchors extend through at least some of the second plurality of windows into posterior tissue of the native valve.

6. The annuloplasty device of claim 5, wherein the first plurality of anchors in the first deployed state and the third plurality of anchors in the third deployed state are axially aligned with respect to the tube and offset from one another such that the first plurality of anchors in the first deployed state do not interfere with the third plurality of anchors in the third deployed state.

7. The annuloplasty device of claim 1, wherein the tube further comprises a locking window configured to prevent the at least one anterior anchor from transitioning from the first constrained state to the first deployed state.

8. The annuloplasty device of claim 7, wherein the first elongated base comprises a first void biased to reduce in size and a protrusion adjacent to the first void comprising a first portion and a second portion separated by a second void, and wherein the anterior anchor further comprises a pulley configured to move within the first void from a first position configured to cause the first void to expand in size to a second position configured to permit the first void to reduce in size.

9. The annuloplasty device of claim 8, wherein, when the pulley is in the first position, the first and second portions of the protrusion are caused to extend into the locking window of the tube and to move apart from one another and, when the pulley is in the second position, the first and second portions of the protrusion are caused to retract from the locking window and move toward one another permitting the pulley to move with respect to the tube thereby causing the first plurality of anchors to extend through at least some of the plurality of windows and into tissue of the native valve site.

10. The annuloplasty device of claim 8, further comprising a pulley activator in mechanical communication with the pulley and a handle positioned extracorporeally and configured to selectively transition the pulley from the first position to the second position.

11. The annuloplasty device of claim 1, wherein the at least one first anchor is substantially linear and is positioned at an end of the first elongated base.

12. The annuloplasty device of claim 1, further comprising a lock having a first engagement configured to engage the first end with the second end and a second engagement configured to selectively disengage the first end and the second end.

13. The annuloplasty device of claim 1, wherein the tube comprises an inner layer comprising a polymer and an outer layer comprising a fabric.

14. An annuloplasty device comprising:
   a tube comprising an inner lumen, a plurality of windows, and a locking window, the tube configured to form a ring shape upon delivery to a native valve site of a patient;
   at least one anchor comprising an elongated base, a plurality of anchors extending from the elongated base, a first void biased to reduce in size, and a protrusion adjacent to the first void and comprising a first portion and a second portion separated by a second void; and
   a pulley configured to move within the first void from a first position configured to cause the first void to expand in size to a second position configured to permit the first void to reduce in size,
   wherein, when the pulley is in the first position, the first and second portions of the protrusion are caused to extend into the locking window of the tube and to move apart from one another and, when the pulley is in the second position, the first and second portions of the protrusion are caused to retract from the locking window and move toward one another permitting the pulley to move with respect to the tube thereby causing the plurality of anchors to extend through at least some of the plurality of windows and into tissue of the native valve site.

15. The annuloplasty device of claim 14, wherein a base of the protrusion comprises an indention configured to receive a portion of the pulley and to resist movement of the pulley from the first position to the second position.

16. The annuloplasty device of claim 14, wherein each anchor of the plurality of anchors has a first shape, and the at least one anchor further comprises at least one secondary anchor extending from the first elongated base and having a second shape different than the first shape.

17. The annuloplasty device of claim 16, wherein the at least one secondary anchor is positioned at an end of the end of at least one anchor.

18. The annuloplasty device of claim 16, wherein the first shape is curved and the second shape is substantially linear.

19. The annuloplasty device of claim 14, further comprising:
   at least one second anchor comprising a second elongated base, a plurality of second anchors extending from the second elongated base, a third void biased to reduce in size, and a second protrusion adjacent to the third void and comprising a third portion and a fourth portion separated by a fourth void; and a second pulley configured to move within the third void from a third position configured to cause the third void to expand in size to a fourth position configured to permit the third void to reduce in size.

20. The annuloplasty device of claim 19, wherein the tube further comprises a second locking window and wherein, when the second pulley is in the third position, the third and fourth portions of the protrusion are caused to extend into the second locking window of the tube and to move apart from one another and, when the pulley is in the fourth position, the third and fourth portions of the protrusion are caused to retract from the second locking window and move toward one another permitting the second pulley to move with respect to the tube thereby causing the plurality of second anchors to extend through at least some of the plurality of windows and into tissue of the native valve site.

21. The annuloplasty device of claim 19, wherein, when the pulley is in the second position, the at least one anchor is configured to enter anterior tissue of the native valve site and, when the second pulley is in the fourth position, the at least one second anchor is configured to enter posterior tissue of the native valve site.

22. The annuloplasty device of claim 14, wherein the tube further comprises a first end and a second end, the annuloplasty device further comprising a lock having a first engagement configured to engage the first end with the second end and a second engagement configured to selectively disengage the first end and the second end.

23. The annuloplasty device of claim 14, wherein the tube comprises an inner layer comprising a polymer and an outer layer comprising a fabric.

\* \* \* \* \*